United States Patent
Oshima et al.

(10) Patent No.: US 9,539,390 B2
(45) Date of Patent: Jan. 10, 2017

(54) MEDICAL INSTRUMENT

(71) Applicant: SEIKO EPSON CORPORATION, Tokyo (JP)

(72) Inventors: Atsushi Oshima, Kanie-cho (JP); Noritaka Ide, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 491 days.

(21) Appl. No.: 14/019,317

(22) Filed: Sep. 5, 2013

(65) Prior Publication Data

US 2014/0066834 A1 Mar. 6, 2014

(30) Foreign Application Priority Data

Sep. 6, 2012 (JP) .................... 2012-196552
Oct. 19, 2012 (JP) .................... 2012-232219

(51) Int. Cl.
| | | |
|---|---|---|
| *H03B 1/00* | (2006.01) | |
| *A61M 5/172* | (2006.01) | |
| *H01L 27/06* | (2006.01) | |
| *A61M 5/142* | (2006.01) | |

(52) U.S. Cl.
CPC ......... *A61M 5/172* (2013.01); *A61M 5/14232* (2013.01); *H01L 27/0629* (2013.01)

(58) Field of Classification Search
CPC .............. H01L 2924/00; H01L 2924/00014; H01L 2924/0002; H01L 2924/16225; H01L 2924/45144
See application file for complete search history.

(56) References Cited

U.S. PATENT DOCUMENTS

| | | |
|---|---|---|
| 2002/0089798 A1 | 7/2002 | Iwanami |
| 2002/0180814 A1 | 12/2002 | Tamura |
| 2004/0241980 A1* | 12/2004 | Yamazaki ......... G02F 1/136227 438/632 |
| 2009/0303271 A1 | 12/2009 | Tabata et al. |
| 2011/0220979 A1 | 9/2011 | Kawashima et al. |
| 2012/0147580 A1 | 6/2012 | Hayashi |

FOREIGN PATENT DOCUMENTS

| | | |
|---|---|---|
| JP | 06-268341 A | 9/1994 |
| JP | 11-307894 A | 11/1999 |

(Continued)

*Primary Examiner* — Sibin Chen
(74) *Attorney, Agent, or Firm* — Maschoff Brennan

(57) ABSTRACT

A medical instrument includes a multilayer wiring board having first, second and third wirings, a fourth wiring formed in a first wiring layer, and a fifth wiring formed in a second wiring layer. A first via conductor electrically connects the third and fifth wirings. A second via conductor electrically connects the fourth and fifth wirings. The medical instrument further includes first and second transistors, a second transistor, and a capacitor mounted on the first wiring layer side of the multilayer wiring board. The drain and source electrodes of the first transistor are electrically connected to the first and second wirings, respectively. The drain electrode of the second transistor is electrically connected to the second wiring. The source electrode of the second transistor is electrically connected to the third wiring. The first and second electrodes of the capacitor are electrically connected to the first and fourth wirings, respectively.

8 Claims, 17 Drawing Sheets

(56) References Cited

FOREIGN PATENT DOCUMENTS

| | | |
|---|---|---|
| JP | 2000-174443 A | 6/2000 |
| JP | 2002-355970 A | 12/2002 |
| JP | 2006-080168 A | 3/2006 |
| JP | 2008-147573 A | 6/2008 |
| JP | 2009-027140 A | 2/2009 |
| JP | 2011-187809 A | 9/2011 |
| JP | 2014-051016 A | 3/2014 |
| WO | 2007/072945 A1 | 6/2007 |

* cited by examiner

MEDICAL INSTRUMENT

This application claims priority to Japanese Patent Application Nos. 2012-196552 filed on Sep. 6, 2012 and Japanese Patent Application No. 2012-232219 filed on Oct. 19, 2012. The entire disclosure of Japanese Patent Application Nos. 2012-196552 and 2012-232219 is hereby incorporated herein by reference.

BACKGROUND

1. Technical Field

The present invention relates to a semiconductor device, a medical instrument, and the like.

2. Related Art

Similar to an ejecting head which is mounted in an ink jet printer, there are many actuators constituted by a capacitive load, such as a piezoelectric element. In order to drive an actuator as a capacitive load, a drive signal having a certain level of power is required. Accordingly, a drive waveform signal as a source of a drive signal is power-amplified to generate a drive signal. When an analog drive waveform signal is power-amplified in an analog form to directly generate an analog drive signal, significant power loss occurs and power efficiency is degraded. Accordingly, technology for power amplification using a so-called class D amplifier has been suggested.

A medical instrument which uses a fluid transport apparatus, in which a plurality of rollers are provided on a concentric circle of a rim portion of a rotor, a tube is mounted such that a fluid flows between the tube and a tube receiving member, and when the rotor rotates, the rollers sequentially press the tube to cause the fluid to flow, is known. A medical instrument which uses a fluid transport apparatus, in which the tube is pressed to cause the fluid to flow using a plurality of pressing elements (for example, piezoelectric elements) instead of a plurality of rollers, or a medical instrument which uses a fluid ejecting apparatus using a piezoelectric element is also known.

For example, when a switching circuit, such as a class D amplifier, is used as a circuit which drives a plurality of piezoelectric elements, in order to suppress ringing of an output voltage, in general, a bypass capacitor is arranged between a power supply potential and a ground potential (for example, JP-A-2011-187809). In an ink jet printer, the occurrence of ringing leads to the occurrence of EMI noise. As a result, the amount of ink to be ejected varies, thereby causing interference with improvement in printing quality. In a medical instrument using a fluid transport apparatus or a fluid ejecting apparatus, the occurrence of ringing leads to the occurrence of EMI noise, causing interference with the operation of the apparatus itself or peripherals. For example, in a medical instrument using a fluid ejecting apparatus, the occurrence of EMI noise with ringing causes variation in the amount of fluid to be ejected.

In order to suppress ringing, it is important to decrease parasitic inductance in a loop having two transistors and a bypass capacitor of a switching circuit. In order to decrease parasitic inductance, it is necessary to decrease the area of a loop having two transistors and a bypass capacitor of a switching circuit. The inter-electrode distance of the capacitor increases with an increase in capacitance of the capacitor, and thus, in the arrangement of the capacitor described in JP-A-2011-187809, an increase in capacitance of the capacitor results in an increase in the area of the loop. For this reason, there is a limitation to suppress ringing, that is, to improve printing quality or to stably transport a fluid.

SUMMARY

An advantage of some aspects of the invention is that it provides a liquid ejecting apparatus and a printing apparatus capable of ejecting a liquid with high precision, a switching circuit in which the occurrence of ringing is suppressed, a medical instrument which stably handles a fluid, and the like.

Application Example 1

This application example is directed to a liquid ejecting apparatus including a capacitive load drive circuit, in which the capacitive load drive circuit includes a drive waveform generator which generates a drive waveform signal, a modulator which performs pulse modulation on the drive waveform signal to generate a modulated signal, a multilayer wiring board having a first wiring layer and a second wiring layer, and a first transistor, a second transistor, and a capacitor mounted on the first wiring layer side of the multilayer wiring board, a switching circuit which receives the modulated signal on the gate electrode of the first transistor and the gate electrode of the second transistor, and generates an amplified digital signal as a signal obtained through power amplification on the modulated signal, and a low pass filter which smoothes the amplified digital signal to generate a drive signal, the multilayer wiring board has a first wiring, a second wiring, a third wiring, and a fourth wiring formed in the first wiring layer, a fifth wiring formed in the second wiring layer, a first via conductor electrically connecting the first wiring and the fifth wiring, and a second via conductor electrically connecting the fourth wiring and the fifth wiring, the drain electrode of the first transistor is electrically connected to the first wiring, the source electrode of the first transistor is electrically connected to the second wiring, the drain electrode of the second transistor is electrically connected to the second wiring, the source electrode of the second transistor is electrically connected to the third wiring, the first electrode of the capacitor is electrically connected to the fourth wiring, and the second electrode of the capacitor is electrically connected to the third wiring.

According to this application example, the first transistor, the second transistor, and the capacitor are all mounted on the first wiring layer side of the multilayer wiring board, and a loop is electrically formed through the fifth wiring formed in the second wiring layer. Accordingly, even if the capacitor increases, it is possible to suppress an increase in the area of the electrical loop including the first transistor, the second transistor, and the capacitor compared to a case where the capacitor is mounted on the second wiring layer side of the multilayer wiring board. It is also possible to suppress an increase in the area of the electrical loop including the first transistor, the second transistor, and the capacitor compared to a case where all wirings are formed in the same wiring layer. That is, it is possible to suppress an increase in parasitic inductance. Accordingly, it is possible to suppress ringing of the output voltage of the switching circuit. Therefore, it is possible to implement a liquid ejecting apparatus which can eject a liquid with high precision.

Since the first transistor, the second transistor, and the capacitor are all mounted on the first wiring layer side of the multilayer wiring board, it is possible to easily perform mounting.

Since there are no elements arranged on the second wiring layer side of the multilayer wiring board, it becomes easy to take heat radiation measures of the first transistor and the second transistor, for example, a heat sink on the second wiring layer side of the multilayer wiring board.

Application Example 2

In the liquid ejecting apparatus according to the above-described application example, it is preferable that, when the multilayer wiring board is viewed in plan view, at least a part of the first transistor, at least a part of the second transistor, and at least a part of the capacitor are arranged on the same line.

According to this application example, since at least a part of the first transistor, at least a part of the second transistor, and at least a part of the capacitor are arranged on the same line, it is possible to decrease the area of the electrical loop including the first transistor, the second transistor, and the capacitor. Accordingly, since it is possible to decrease parasitic inductance, it is possible to suppress ringing of the output voltage of the switching circuit. Therefore, it is possible to implement a liquid ejecting apparatus which can eject a liquid with high precision.

Application Example 3

In the liquid ejecting apparatus according to the above-described application example, it is preferable that the second wiring and the fifth wiring are formed at positions at least partially overlapping each other when the multilayer wiring board is viewed in plan view.

Usually, reverse currents flow in the second wiring and the fifth wiring. According to this application example, since the second wiring and the fifth wiring are formed at positions at least partially overlapping each other, parasitic inductance decreases by the effect of mutual inductance. Accordingly, it is possible to suppress ringing of the output voltage of the switching circuit. Therefore, it is possible to implement a liquid ejecting apparatus which can eject a liquid with high precision.

Application Example 4

In the liquid ejecting apparatus according to the above-described application example, it is preferable that the multilayer wiring board further has a sixth wiring formed in a wiring layer other than the first wiring layer, and a third via conductor electrically connecting the second wiring and the sixth wiring.

According to this application example, since the sixth wiring electrically connected to the second wiring is formed in a wiring layer (for example, the second wiring layer) other than the first wiring layer, the sixth wiring functions as a heat sink. Therefore, it is possible to improve heat radiation efficiency of the second transistor.

Application Example 5

In the liquid ejecting apparatus according to the above-described application example, it is preferable that the multilayer wiring board further has a seventh wiring formed in the first wiring layer, an eighth wiring formed in the second wiring layer, and a fourth via conductor electrically connecting the second wiring and the eighth wiring, the gate electrode of the first transistor is electrically connected to the seventh wiring, and the seventh wiring and the eighth wiring are formed at positions at least partially overlapping each other when the multilayer wiring board is viewed in plan view.

Usually, reverse currents flow in the seventh wiring and the eighth wiring. According to this application example, since the seventh wiring and the eighth wiring are formed at positions at least partially overlapping each other, parasitic inductance decreases by the effect of mutual inductance. Accordingly, it is possible to suppress ringing of the output voltage of the switching circuit. Therefore, it is possible to implement a liquid ejecting apparatus which can eject a liquid with high precision.

Application Example 6

In the liquid ejecting apparatus according to the above-described application example, it is preferable that the multilayer wiring board has a ninth wiring formed in the first wiring layer, a tenth wiring formed in the second wiring layer, and a fifth via conductor electrically connecting the third wiring and the tenth wiring, the gate electrode of the second transistor is electrically connected to the ninth wiring, and the ninth wiring and the tenth wiring are formed at positions at least partially overlapping each other when the multilayer wiring board is viewed in plan view.

Usually, reverse currents flow in the ninth wiring and the tenth wiring. According to this application example, since the ninth wiring and the tenth wiring are formed at positions at least partially overlapping each other, parasitic inductance decreases by the effect of mutual inductance. Accordingly, it is possible to suppress ringing of the output voltage of the switching circuit. Therefore, it is possible to implement a liquid ejecting apparatus which can eject a liquid with high precision.

Application Example 7

This application example is directed to a printing apparatus including any of the above-described liquid ejecting apparatuses.

According to this application example, since a liquid ejecting apparatus capable of ejecting a liquid with high precision is provided, it is possible to implement a printing apparatus having excellent printing quality.

Application Example 8

This application example is directed to a switching circuit including a multilayer wiring board having a first wiring layer and a second wiring layer, and a first transistor, a second transistor, and a capacitor mounted on the first wiring layer side of the multilayer wiring board, in which the multilayer wiring board has a first wiring, a second wiring, a third wiring, and a fourth wiring formed in the first wiring layer, a fifth wiring formed in the second wiring layer, a first via conductor electrically connecting the third wiring and the fifth wiring, and a second via conductor electrically connecting the fourth wiring and the fifth wiring, the drain electrode of the first transistor is electrically connected to the first wiring, the source electrode of the first transistor is electrically connected to the second wiring, the drain electrode of the second transistor is electrically connected to the second wiring, the source electrode of the second transistor is electrically connected to the third wiring, the first electrode of the capacitor is electrically connected to the first wiring, and the second electrode of the capacitor is electrically connected to the fourth wiring.

According to this application example, the first transistor, the second transistor, and the capacitor are all mounted on the first wiring layer side of the multilayer wiring board, and form an electrical loop through the fifth wiring formed in the second wiring layer. Accordingly, even if the capacitor increases, it is possible to suppress an increase in the area of the electrical loop including the first transistor, the second transistor, and the capacitor compared to a case where the capacitor is mounted on the second wiring layer side of the multilayer wiring board. It is also possible to suppress an increase in the area of the electrical loop including the first transistor, the second transistor, and the capacitor compared to a case where all wirings are formed in the same wiring layer. That is, it is possible to suppress an increase in parasitic inductance. Therefore, it is possible to suppress ringing of the output voltage of the switching circuit.

Since the first transistor, the second transistor, and the capacitor are all mounted on the first wiring layer side of the multilayer wiring board, it is possible to easily perform mounting.

Since there are no elements arranged on the second wiring layer side of the multilayer wiring board, it becomes easy to take heat radiation measures of the first transistor and the second transistor, for example, a heat sink on the second wiring layer side of the multilayer wiring board.

Application Example 9

In the switching circuit according to the above-described application example, it is preferable that, when the multilayer wiring board is viewed in plan view, at least a part of the first transistor, at least a part of the second transistor, and at least a part of the capacitor are arranged on the same line.

According to this application example, since at least a part of the first transistor, at least a part of the second transistor, and at least a part of the capacitor are arranged on the same line, it is possible to decrease the area of the electrical loop including the first transistor, the second transistor, and the capacitor. Accordingly, since it is possible to decrease parasitic inductance, it is possible to suppress ringing of the output voltage of the switching circuit.

Application Example 10

In the switching circuit according to the above-described application example, it is preferable that the second wiring and the fifth wiring are formed at positions at least partially overlapping each other when the multilayer wiring board is viewed in plan view.

Usually, reverse currents flow in the second wiring and the fifth wiring. According to this application example, since the second wiring and the fifth wiring are formed at positions at least partially overlapping each other, parasitic inductance decreases by the effect of mutual inductance. Accordingly, it is possible to suppress ringing of the output voltage of the switching circuit.

Application Example 11

In the switching circuit according to the above-described application example, it is preferable that the multilayer wiring board further has a sixth wiring formed in a wiring layer other than the first wiring layer, and a third via conductor electrically connecting the first wiring and the sixth wiring.

According to this application example, since the sixth wiring electrically connected to the first wiring is formed in a wiring layer (for example, the second wiring layer) other than the first wiring layer, the sixth wiring functions as a heat sink. Accordingly, it is possible to improve heat radiation efficiency of the first transistor.

Application Example 12

In the switching circuit according to the above-described application example, it is preferable that the multilayer wiring board further has a seventh wiring formed in a wiring layer other than the first wiring layer, and a fourth via conductor electrically connecting the second wiring and the seventh wiring.

According to this application example, since the seventh wiring electrically connected to the second wiring is formed in a wiring layer (for example, the second wiring layer) other than the first wiring layer, the seventh wiring functions as a heat sink. Accordingly, it is possible to improve heat radiation efficiency of the second transistor.

Application Example 13

In the switching circuit according to the above-described application example, it is preferable that the multilayer wiring board further has an eighth wiring formed in the first wiring layer, a ninth wiring formed in the second wiring layer, and a fifth via conductor electrically connecting the second wiring and the ninth wiring, the gate electrode of the first transistor is electrically connected to the eighth wiring, and the eighth wiring and the ninth wiring are formed at positions at least partially overlapping each other when the multilayer wiring board is viewed in plan view.

Usually, reverse currents flow in the eighth wiring and the ninth wiring. According to this application example, since the eighth wiring and the ninth wiring are formed at positions at least partially overlapping each other, parasitic inductance decreases by the effect of mutual inductance. Accordingly, it is possible to suppress ringing of the output voltage of the switching circuit.

Application Example 14

In the switching circuit according to the above-described application example, it is preferable that the multilayer wiring board further has a tenth wiring formed in the first wiring layer, the gate electrode of the second transistor is electrically connected to the tenth wiring, and the fifth wiring and the tenth wiring are formed at positions at least partially overlapping each other when the multilayer wiring board is viewed in plan view.

Usually, reverse currents flow in the fifth wiring and the tenth wiring. According to this application example, since the fifth wiring and the tenth wiring are formed at positions at least partially overlapping each other, parasitic inductance decreases by the effect of mutual inductance. Accordingly, it is possible to suppress ringing of the output voltage of the switching circuit.

Application Example 15

This application example is directed to a medical instrument including a capacitive load drive circuit, in which the capacitive load drive circuit includes a drive waveform generator which generates a drive waveform signal, a modulator which performs pulse modulation on the drive waveform signal to generate a modulated signal, the above-described switching circuit which receives the modulated signal on the gate electrode of the first transistor and the gate electrode of the second transistor, and generates an amplified digital signal as a signal obtained through power amplification on the modulated signal, and a low pass filter which smoothes the amplified digital signal to generate a drive signal.

According to this application example, since a switching circuit in which the occurrence of ringing is suppressed is provided, it is possible to implement a medical instrument which can stably handle a fluid.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
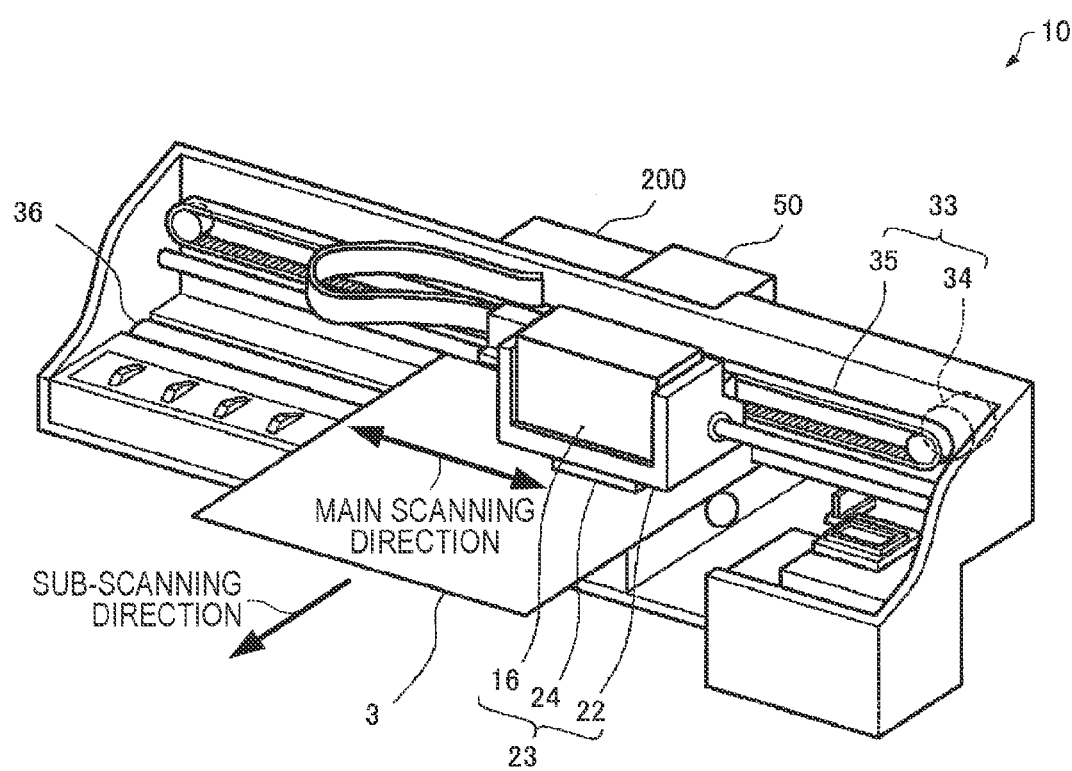
FIG. 1 is an explanatory view showing a configuration example of an ink jet printer as an example of a printing apparatus.

Hereinafter, a preferred embodiment of the invention will be described in detail referring to the drawings. The drawings to be used are for convenience of description. The following embodiment is not intended to unduly limit the content of the invention described in the appended claims. It is not always true that the entire configuration described below is the essential constituent requirement of the invention.

Hereinafter, an embodiment of the invention will be described in the following sequence.

1. Configuration example of printing apparatus and liquid ejecting apparatus
2. Circuit configuration of capacitive load drive circuit
3. Arrangement example of switching circuit
4. First modification of arrangement example of switching circuit
5. Second modification of arrangement example of switching circuit
6. Third modification of arrangement example of switching circuit
7. Fourth modification of arrangement example of switching circuit
8. Fifth modification of arrangement example of switching circuit
9. Medical instrument 1. Configuration Example of Printing Apparatus and Liquid Ejecting Apparatus FIG. 1 is an explanatory view showing a configuration example of an ink jet printer 10 as an example of a printing apparatus. The ink jet printer 10 includes a carriage 23 which forms ink dots on a printing medium 3 while reciprocating in a main scanning direction, a drive mechanism 33 which reciprocates the carriage 23, a platen roller 36 which feeds the printing medium 3, and the like. The carriage 23 is provided with an ink cartridge 16 which stores ink, a carriage case 22 in which the ink cartridge 16 is mounted, an ejecting head 24 which is mounted on the bottom side (the side facing the printing medium 3) of the carriage case 22 and ejects ink, and the like. Ink in the ink cartridge 16 is guided to the ejecting head 24 and ejected from the ejecting head 24 onto the printing medium 3 to print an image.

The drive mechanism 33 which reciprocates the carriage 23 includes a timing belt 35 which is stretched by pulleys, a stepping motor 34 which drives the timing belt 35 through the pulleys, and the like. A part of the timing belt 35 is fixed to the carriage case 22, and the timing belt 35 is driven to reciprocate the carriage case 22. The platen roller 36 constitutes a sheet feed mechanism, which feeds the printing medium 3, along with a drive motor or a gear mechanism (not shown), and can feed the printing medium 3 by a predetermined amount in a sub-scanning direction.

In the ink jet printer 10, a printer control circuit 50 which controls the entire operation, and a capacitive load drive circuit 200 which drives the ejecting head 24 are mounted. The printer control circuit 50 controls the entire operation in which the capacitive load drive circuit 200, the drive mechanism 33, the sheet feed mechanism, and the like drive the ejecting head 24 to eject ink while feeding the printing medium 3.

Figure 2:
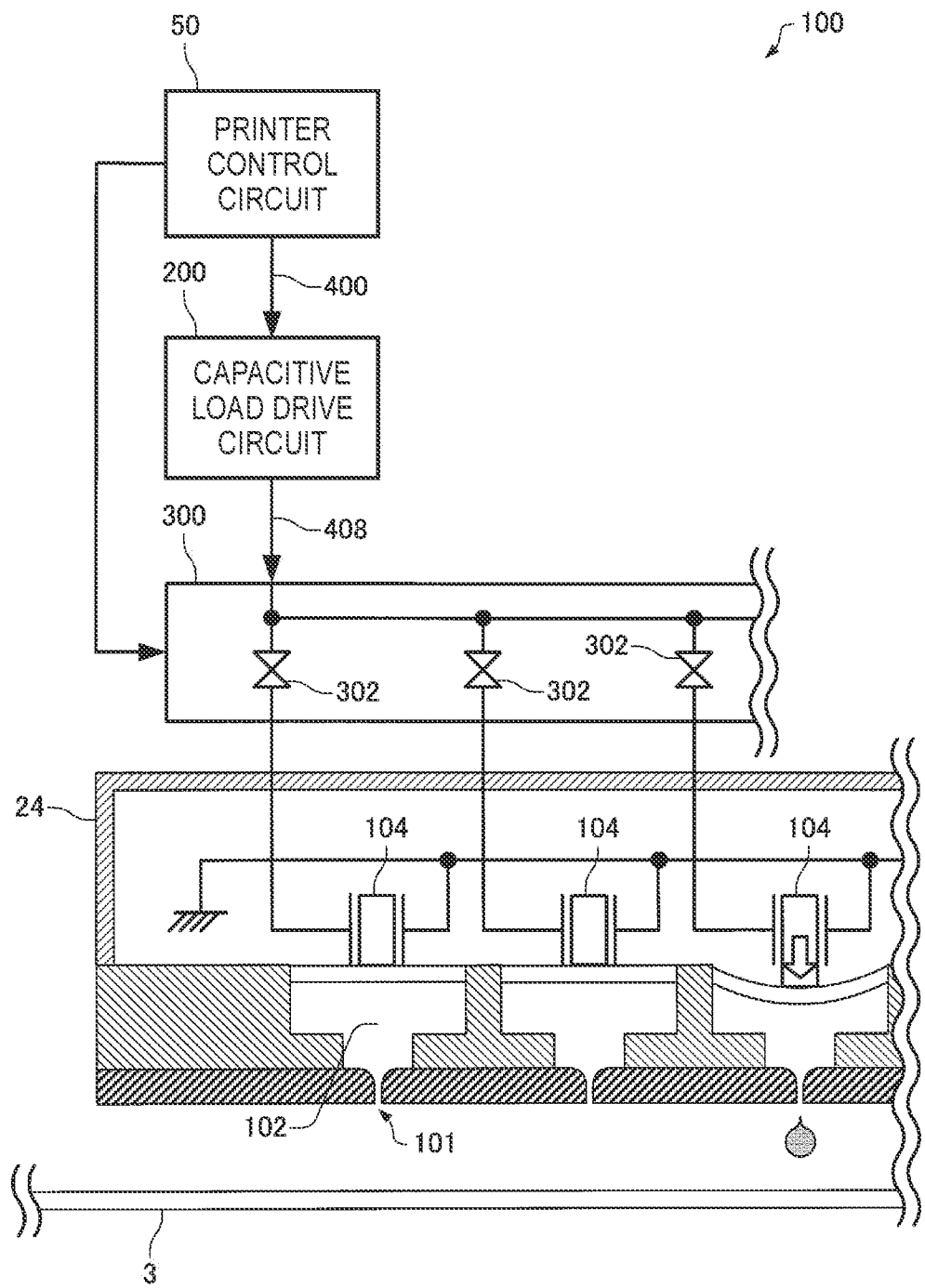
FIG. 2 is an explanatory view showing a configuration example of a liquid ejecting apparatus in the ink jet printer.

FIG. 2 is an explanatory view showing a configuration example of a liquid ejecting apparatus 100 in the ink jet printer 10. FIG. 2 shows an aspect in which the capacitive load drive circuit 200 drives the ejecting head 24 under the control of the printer control circuit 50. First, the internal structure of the ejecting head 24 will be simply described. As shown in the drawing, a plurality of ejecting ports 101 through which ink droplets are ejected are provided at the bottom of the ejecting head 24 facing the printing medium 3. Each ejecting port 101 is connected to an ink chamber 102, and ink supplied from the ink cartridge 16 is filled in the ink chamber 102. A piezoelectric element 104 is provided above each ink chamber 102. If a voltage is applied to the piezoelectric element 104, the piezoelectric element 104 is deformed to pressurize the ink chamber 102, and ink is ejected from the ejecting port 101. The piezoelectric element 104 changes in deformation amount depending on a voltage value to be applied. An appropriate voltage waveform is applied to the piezoelectric element 104 to control the deformation amount or timing of the ink chamber 102, whereby an appropriate amount of ink can be ejected at an appropriate timing.

A drive signal 408 which is a voltage to be applied to the piezoelectric element 104 is generated on the basis of a control signal 400 from the printer control circuit 50 by the capacitive load drive circuit 200. The generated drive signal 408 is supplied to the piezoelectric element 104 through a gate unit 300. The gate unit 300 is a circuit unit in which a plurality of gate elements 302 are connected in parallel, and each gate element 302 can be individually placed in a conduction state or a disconnection state under the control of the printer control circuit 50. Accordingly, the drive signal 408 output from the capacitive load drive circuit 200 passes through the gate element 302 set in the conduction state in advance by the printer control circuit 50 and applied to the corresponding piezoelectric element 104, and ink is ejected from the ejecting port 101.

2. Circuit Configuration of Capacitive Load Drive Circuit

Figure 3:
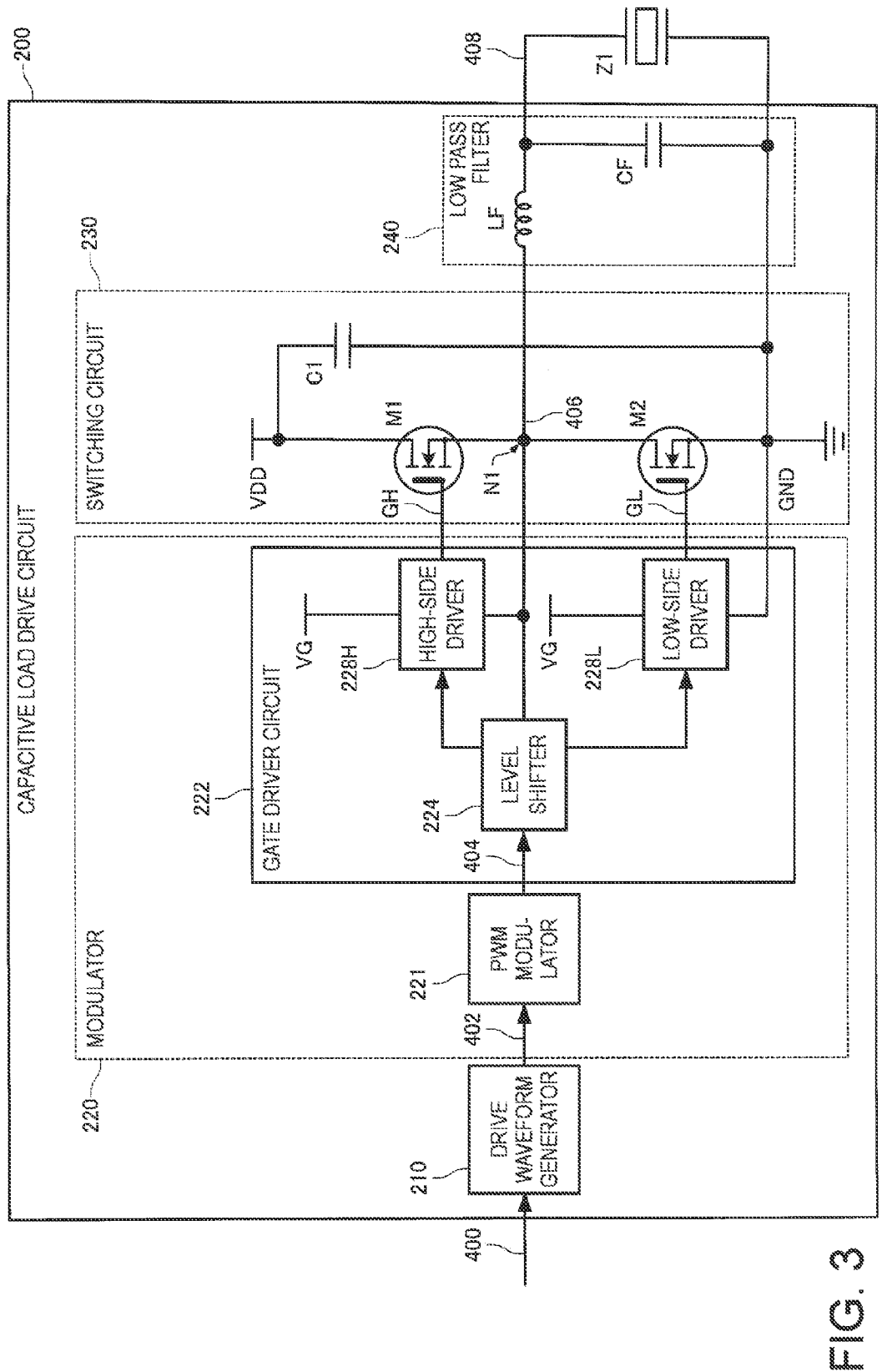
FIG. 3 is an explanatory view showing the detailed configuration of a capacitive load drive circuit of this embodiment.

FIG. 3 is an explanatory view showing the detailed configuration of the capacitive load drive circuit 200 of this embodiment. As shown in the drawing, capacitive load drive circuit 200 includes a drive waveform generator 210 which generates a drive waveform signal 402, a modulator 220 which performs pulse modulation on the drive waveform signal 402 to generate a modulated signal GH and a modulated signal GL, a switching circuit 230 which receives the modulated signal GH and the modulated signal GL, and generates an amplified digital signal 406 which is a signal by performing power amplification on the modulated signal GH and the modulated signal GL, and a low pass filter 240 which smoothes the amplified digital signal 406 to generate the drive signal 408. A capacitive load Z1 to which the drive signal 408 is applied corresponds to the piezoelectric element 104 shown in FIG. 2.

The drive waveform generator 210 generates a drive waveform signal 402 as a reference of the drive signal 408 on the basis of the control signal 400.

The modulator 220 includes a PWM modulator 221 which performs PWM modulation (pulse-width modulation) on the drive waveform signal 402 to generate a PWM modulated signal 404, and a gate driver circuit 222 which generates the modulated signal GH and the modulated signal GL on the basis of the PWM modulated signal 404.

The gate driver circuit 222 includes a level shifter 224 which adjusts the level of the PWM modulated signal 404, a high-side driver 228H which switches the ON/OFF of a first transistor M1 on the basis of the PWM modulated signal 404 through the level shifter 224, and a low-side driver 228L which switches the ON/OFF of a second transistor M2 on the basis of the PWM modulated signal 404 through the level shifter 224.

A signal which is output from the high-side driver 228H when switching the ON/OFF of the first transistor M1 is defined as the modulated signal GH, and a signal which is output from the low-side driver 228L when switching the ON/OFF of the second transistor M2 is defined as the modulated signal GL.

The switching circuit 230 is constituted as a digital power amplifier including the first transistor M1 and the second transistor M2 which generate the amplified digital signal 406, and a capacitor C1 which functions as a bypass capacitor. In the capacitive load drive circuit 200 of this embodiment, although the first transistor M1 and the second transistor M2 are N-type MOSFETs, for example, other kinds of elements, such as an insulated gate bipolar transistor (IGBT), may be used. As a switching circuit to which the invention is applied, there are various switching circuits including a switching amplifier circuit, a switching power supply circuit, a motor drive circuit, and an inverter circuit.

As shown in FIG. 3, the first transistor M1 and the second transistor M2 are connected between a potential VDD (hereinafter, simply referred to as VDD) to be supplied from the power supply and a ground potential GND (hereinafter, simply referred to as GND). The amplified digital signal 406 is generated by switching the ON/OFF of the first transistor M1 and the second transistor M2. A contact (node) at which the first transistor M1 and the second transistor M2 are connected is defined as a first node N1. The first node N1 is on a wiring through which the amplified digital signal 406 is transmitted. The capacitor C1 is connected between VDD and GND.

The low pass filter 240 removes a high-frequency component of the amplified digital signal 406 to generate the drive signal 408. In the example shown in FIG. 3, the low pass filter 240 is constituted as a low pass filter including a coil LF and a capacitor CF.

Figure 4:
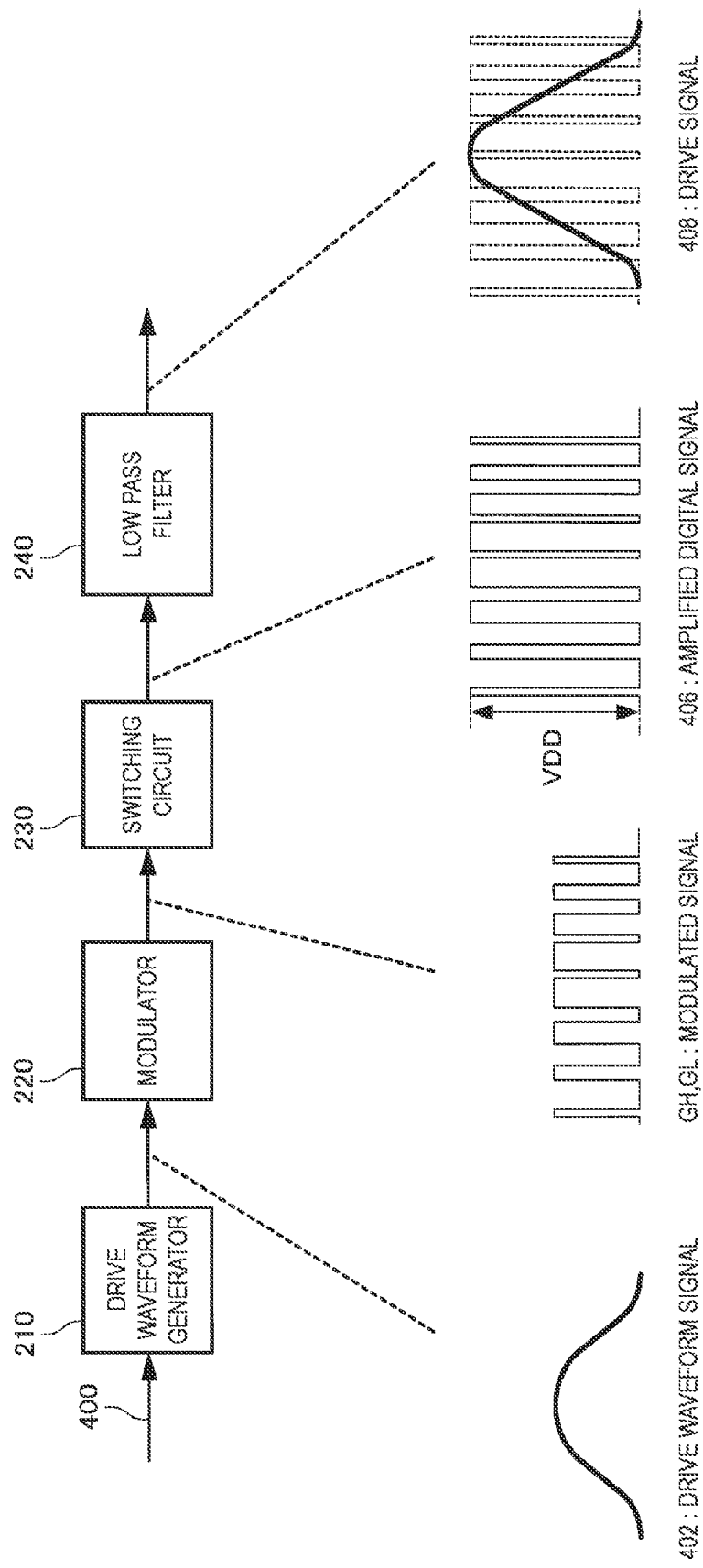
FIG. 4 is an explanatory view showing the outline of an operation of the capacitive load drive circuit to generate a drive signal.

FIG. 4 is an explanatory view showing the outline of an operation of the capacitive load drive circuit 200 to generate the drive signal 408. For example, the drive waveform generator 210 generates the drive waveform signal 402 shown in FIG. 4 on the basis of the control signal 400. The drive waveform signal 402 is not limited to an analog signal shown in FIG. 4, and for example, a signal output at DC level or a multibit digital signal may be used.

The drive waveform generator 210 may include, for example, an arithmetic unit and may compute the drive waveform signal 402 on the basis of the control signal 400. The drive waveform generator 210 may include, for example, a waveform memory which stores a waveform, and may generate the drive waveform signal 402 corresponding to the control signal 400 with reference to the waveform memory.

If the drive waveform signal 402 from the drive waveform generator 210 is received, the modulator 220 performs predetermined modulation to generate the modulated signal GH and the modulated signal GL. In this embodiment, although the predetermined modulation is pulse-width modulation (PWM), for example, other modulation systems, such as pulse-density modulation (PDM), may be used.

The switching circuit 230 receives the modulated signal GH and the modulated signal GL, and performs power amplification. As shown in FIG. 3, the switching circuit 230 amplifies power using the first transistor M1 and the second transistor M2. In the example shown in FIG. 4, the switching circuit 230 generates the amplified digital signal 406 in which the voltage of the PWM modulated signal 404 is amplified to VDD.

The low pass filter 240 smoothes the amplified digital signal 406 to generate the analog drive signal 408 in which a portion modulated to a wide pulse width has a high voltage value, and a portion modulated to a narrow pulse width has a low voltage value. As shown in FIG. 3, the low pass filter 240 can be easily implemented by combining the coil LF and the capacitor CF.

In the capacitive load drive circuit 200 of this embodiment, since the switching circuit 230 switches the ON/OFF of the first transistor M1 and the second transistor M2 to amplify power, there is no case where extra power is consumed. The low pass filter 240 may be constituted by components, such as the coil LF and the capacitor CF, which do not consume power. For this reason, since it is possible to significantly reduce power loss compared to a case where, like a so-called analog amplifier circuit, power amplification is performed on the analog drive waveform signal 402 in an analog form, it is possible to significantly reduce power loss when generating the drive signal 408.

In the switching circuit 230, ringing of the output voltage may become problematic. If ringing occurs, since EMI noise occurs, there is an interference with the operation of the apparatus itself or peripherals. When the rising time of the switching waveform is extended so as to suppress ringing, power efficiency is degraded, and fluid control precision is degraded. If ringing occurs, a voltage which is applied to the first transistor M1 and the second transistor M2 increases, causing element breakdown or erroneous operation.

As the factor for the occurrence of ringing, there is a resonance phenomenon by parasitic inductance of the electrical loop including the first transistor M1, the second transistor M2, and the capacitor C1 and parasitic capacitance between the drain and source of the first transistor M1 or the second transistor M2, a resonance phenomenon by parasitic inductance of the electrical loop including the high-side driver 228H and the first transistor M1 and gate capacitance of the first transistor M1, a resonance phenomenon by parasitic inductance of the electrical loop including the low-side driver 228L and the second transistor M2 and gate capacitance of the second transistor M2, or the like.

Accordingly, when arranging elements constituting the switching circuit 230 or wirings, in particular, it is important to decrease parasitic inductance of the electrical loop.

3. Arrangement Example of Switching Circuit

The switching circuit 230 of this embodiment includes a multilayer wiring board 1000 having a first wiring layer and a second wiring layer, and the first transistor M1, the second transistor M2, and the capacitor C1 mounted on the first wiring layer side of the multilayer wiring board 1000.

Figure 5A:
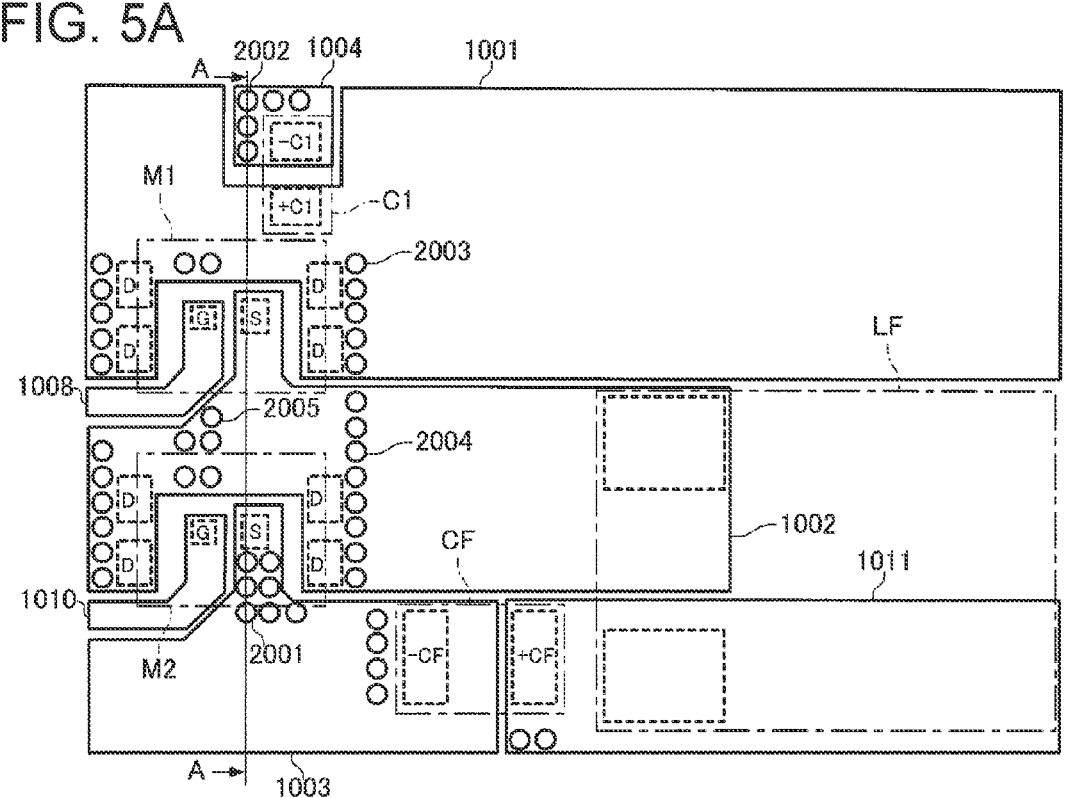
FIGS. 5A and 5B are plan views showing an arrangement example of a switching circuit.
Figure 5B:
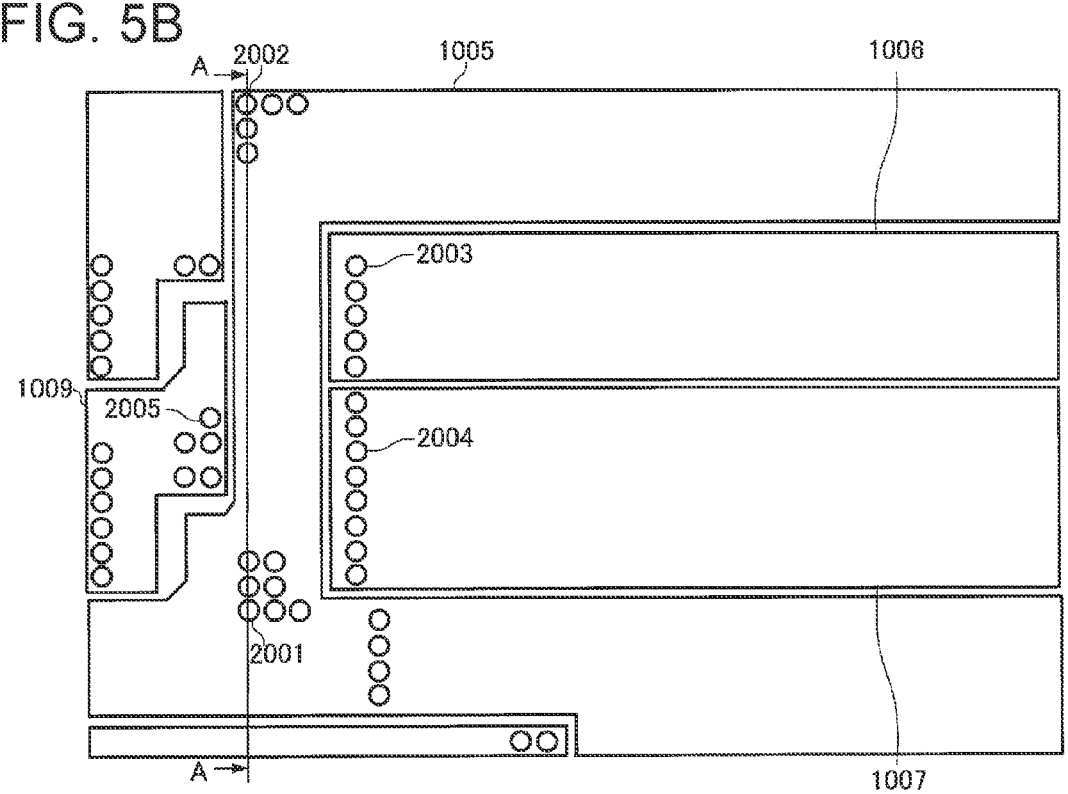

FIGS. 5A and 5B are plan views showing an arrangement example of the switching circuit 230. FIG. 5A primarily shows the configuration of the first wiring layer. FIG. 5B primarily shows the configuration of the second wiring layer. In FIGS. 5A and 5B, a solid polygon represents a wiring formed in the first wiring layer or the second wiring layer, and a solid circle represents the position of a via conductor which electrically connects a wiring of the first wiring layer and a wiring of the second wiring layer. In FIG. 5A, a one-dot-chain line represents the mounting position of each transistor, the capacitor, or the coil, and a dotted line represents the position of an electrode of each transistor, the capacitor, or the coil.

Figure 6:
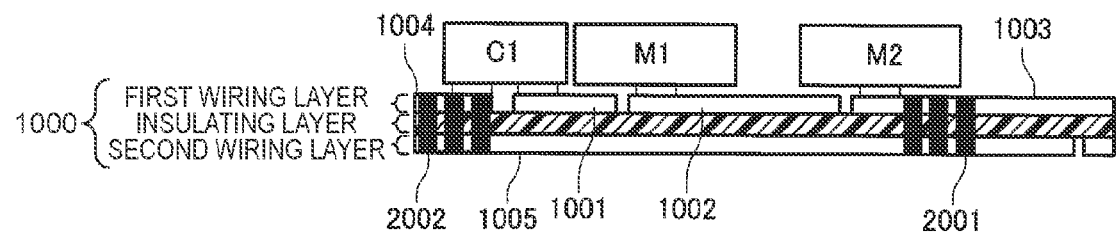
FIG. 6 is a sectional view taken along the line A-A of FIGS. 5A and 5B.

FIG. 6 is a sectional view taken along the line A-A of FIGS. 5A and 5B. As shown in FIG. 6, an insulating layer is provided between the first wiring layer and the second wiring layer of the multilayer wiring board 1000. That is, a wiring formed in the first wiring layer and a wiring formed in the second wiring layer are insulated from each other, except for connection by a via conductor. Usually, the thickness of the insulating layer is sufficiently smaller than the wiring width. The multilayer wiring board 1000 has three or more wiring layers, and two wiring layers arbitrarily selected from among the three or more wiring layers may be the first wiring layer and the second wiring layer. It is preferable that the first wiring layer and the second wiring layer are wiring layers closest to each other. The multilayer wiring board 1000 may have a protective layer which protects a wiring layer.

The multilayer wiring board 1000 of this embodiment has a first wiring 1001, a second wiring 1002, a third wiring 1003, and a fourth wiring 1004 formed in the first wiring layer, a fifth wiring 1005 formed in the second wiring layer, a first via conductor 2001 which electrically connects the third wiring 1003 and the fifth wiring 1005, and a second via conductor 2002 which electrically connects the fourth wiring 1004 and the fifth wiring 1005.

A drain electrode D of the first transistor M1 is electrically connected to the first wiring 1001, and a source electrode S of the first transistor M1 is electrically connected to the second wiring 1002. A drain electrode D of the second transistor M2 is electrically connected to the second wiring 1002, and a source electrode S of the second transistor M2 is electrically connected to the third wiring 1003. A first electrode +C1 of the capacitor C1 is electrically connected to the first wiring 1001, and a second electrode −C1 of the capacitor C1 is electrically connected to the fourth wiring 1004. That is, a part of a wiring path from the source electrode S of the second transistor M2 to the second electrode −C1 of the capacitor C1 is formed as the fifth wiring 1005 of the second wiring layer.

According to this embodiment, since the first transistor M1, the second transistor M2, and the capacitor C1 are all mounted on the first wiring layer side of the multilayer wiring board 1000, and electrically form a loop through the fifth wiring 1005 formed in the second wiring layer, the area of the electrical loop significantly depends on the inter-layer distance between the first wiring layer and the second wiring layer, that is, the thickness of the insulating layer. Accordingly, even if the capacitor C1 increases, it is possible to suppress an increase in the area of the electrical loop including the first transistor M1, the second transistor M2, and the capacitor C1 compared to a case where the capacitor C1 is mounted on the second wiring layer side of the multilayer wiring board 1000. Since the thickness of the insulating layer is sufficiently smaller than the wiring width, it is possible to suppress an increase in the area of the electrical loop including the first transistor M1, the second transistor M2, and the capacitor C1 compared to a case where all wirings are formed in the same wiring layer. That is, it is possible to suppress an increase in parasitic inductance. Accordingly, it is possible to suppress ringing of the output voltage of the switching circuit 230. Therefore, it is possible to implement the liquid ejecting apparatus 100 which can eject a liquid with high precision.

Since the first transistor M1, the second transistor M2, and the capacitor C1 are all mounted on the first wiring layer side of the multilayer wiring board 1000, it is possible to easily perform mounting.

Since the elements are not arranged on the second wiring layer side of the multilayer wiring board 1000, it becomes easy to take heat radiation measures of the first transistor M1 and the second transistor M2, for example, a heat sink on the second wiring layer side of the multilayer wiring board 1000.

In the example shown in FIG. 5A, when the multilayer wiring board 1000 is viewed in plan view, at least a part of the first transistor M1, at least a part of the second transistor M2, and at least a part of the capacitor C1 are arranged on the same line. In the example shown in FIGS. 5A and 6, the capacitor C1, the first transistor M1, and the second transistor M2 are arranged on the same line in this order.

According to this embodiment, since at least a part of the first transistor M1, at least a part of the second transistor M2, and at least a part of the capacitor C1 are arranged on the same line, it is possible to decrease the area of the electrical loop including the first transistor M1, the second transistor M2, and the capacitor C1. Accordingly, since it is possible to decrease parasitic inductance, it is possible to suppress ringing of the output voltage of the switching circuit 230. Therefore, it is possible to implement the liquid ejecting apparatus 100 which can eject a liquid with high precision.

In the example shown in FIGS. 5A and 5B, the second wiring 1002 and the fifth wiring 1005 are formed at position at least partially overlapping each other when the multilayer wiring board 1000 is viewed in plan view.

Figure 7:
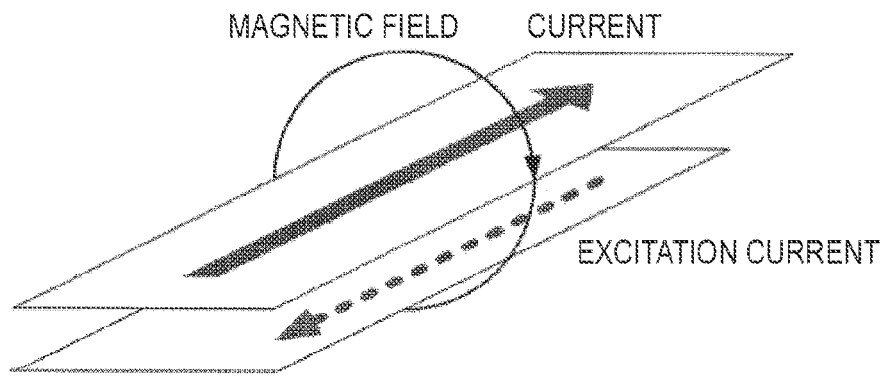
FIG. 7 is a diagram illustrating parasitic inductance.

FIG. 7 is a diagram illustrating parasitic inductance. FIG. 7 shows two wirings which are provided to be separated from each other. If a current flows in one wiring, a counter electromotive force is generated in a direction of cancelling a magnetic field by the current. When two wirings are provided to be close to each other, a counter electromotive force is generated in the other wiring in a direction of cancelling a magnetic field by a current flowing in one wiring (the effect of mutual inductance). Accordingly, it is possible to reduce parasitic inductance of wiring by providing wiring such that currents flowing in two wirings are reverse currents.

Usually, reverse currents flow in the second wiring 1002 and the fifth wiring 1005. According to this embodiment, since the second wiring 1002 and the fifth wiring 1005 are formed at positions at least partially overlapping each other, parasitic inductance decreases by the effect of mutual inductance described referring to FIG. 7. Accordingly, it is possible to suppress ringing of the output voltage of the switching circuit 230. Therefore, it is possible to implement the liquid ejecting apparatus 100 which can eject a liquid with high precision.

In the example shown in FIGS. 5A and 5B, the multilayer wiring board 1000 further has a sixth wiring 1006 formed in the second wiring layer as a wiring layer other than the first wiring layer, and a third via conductor 2003 which electrically connects the first wiring 1001 and the sixth wiring 1006.

According to this embodiment, since the sixth wiring 1006 electrically connected to the first wiring 1001 is formed in a wiring layer (for example, the second wiring layer) other than the first wiring layer, the sixth wiring 1006 functions as a heat sink. Accordingly, it is possible to improve heat radiation efficiency of the first transistor M1.

In the example shown in FIGS. 5A and 5B, the multilayer wiring board 1000 further has a seventh wiring 1007 formed in a wiring layer other than the first wiring layer, and a fourth via conductor 2004 which electrically connects the second wiring 1002 and the seventh wiring 1007.

According to this embodiment, since the seventh wiring 1007 electrically connected to the second wiring 1002 is formed in a wiring layer (for example, the second wiring layer) other than the first wiring layer, the seventh wiring 1007 functions as a heat sink. Accordingly, it is possible to improve heat radiation efficiency of the second transistor M2.

In the example shown in FIGS. 5A and 5B, multilayer wiring board 1000 further has an eighth wiring 1008 formed in the first wiring layer, a ninth wiring 1009 formed in the second wiring layer, and a fifth via conductor 2005 which electrically connects the second wiring 1002 and the ninth wiring 1009, a gate electrode G of the first transistor M1 is electrically connected to the eighth wiring 1008, and the eighth wiring 1008 and the ninth wiring 1009 are formed at positions at least partially overlapping each other when the multilayer wiring board 1000 is viewed in plan view.

Usually, reverse currents flow in the eighth wiring 1008 and the ninth wiring 1009. According to this embodiment, since the eighth wiring 1008 and the ninth wiring 1009 are formed at positions at least partially overlapping each other, parasitic inductance decreases by the effect of mutual inductance described referring to FIG. 7. Accordingly, it is possible to suppress ringing of the output voltage of the switching circuit 230. Therefore, it is possible to implement the liquid ejecting apparatus 100 which can eject a liquid with high precision.

In the example shown in FIGS. 5A and 5B, the multilayer wiring board 1000 further has a tenth wiring 1010 formed in the first wiring layer, a gate electrode G of the second transistor M2 is electrically connected to the tenth wiring 1010, and the fifth wiring 1005 and the tenth wiring 1010 are formed at positions at least partially overlapping each other when the multilayer wiring board 1000 is viewed in plan view.

Usually, reverse currents flow in the fifth wiring 1005 and the tenth wiring 1010. According to this embodiment, since the fifth wiring 1005 and the tenth wiring 1010 are formed at positions at least partially overlapping each other, parasitic inductance decreases by the effect of mutual inductance described referring to FIG. 7. Accordingly, it is possible to suppress ringing of the output voltage of the switching circuit 230. Therefore, it is possible to implement the liquid ejecting apparatus 100 which can eject a liquid with high precision.

In the example shown in FIGS. 5A and 5B, the multilayer wiring board 1000 further has an eleventh wiring 1011 which is formed in the first wiring layer and electrically connected to a first electrode +CF (a positive potential-side electrode) of the capacitor CF, and the fifth wiring 1005 and the eleventh wiring 1011 are formed at positions at least partially overlapping each other when the multilayer wiring board 1000 is viewed in plan view.

When common mode noise lies on the output signal of the capacitive load drive circuit 200, a component of common mode noise appears as a current component in the same direction in the fifth wiring 1005 and the eleventh wiring 1011. According to this embodiment, since the fifth wiring 1005 and the eleventh wiring 1011 are formed at positions at least partially overlapping each other, the effect of mutual inductance described referring to FIG. 7 acts in a direction of cancelling common mode noise. Accordingly, it is possible to suppress common mode noise. It is also possible to suppress EMI noise due to common mode noise.

Figure 8A:
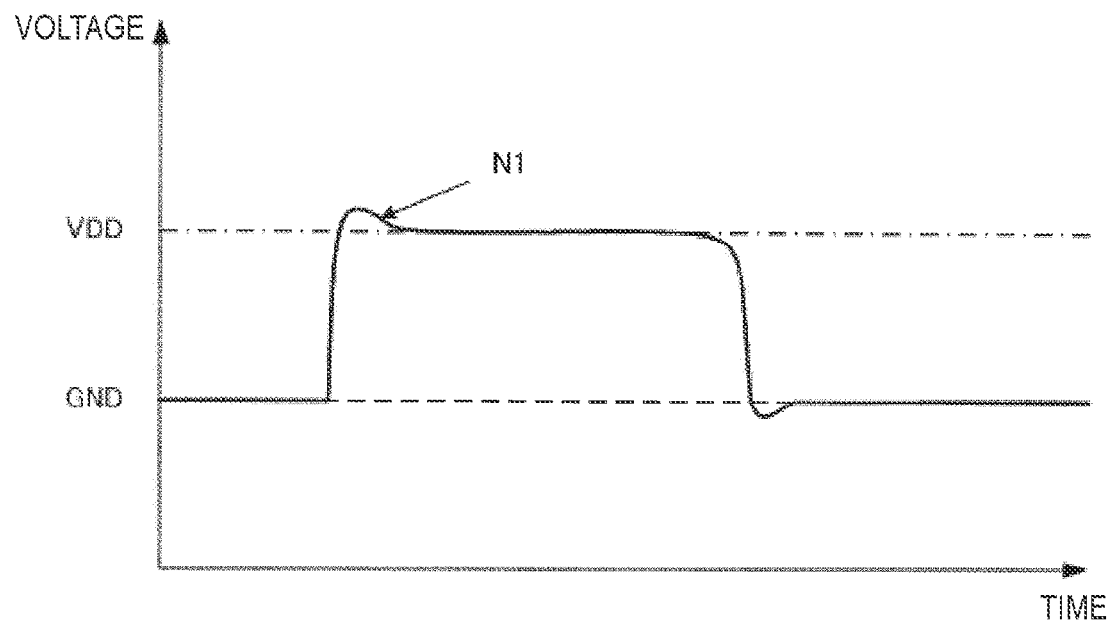
FIG. 8A is a graph showing an output voltage waveform example of the switching circuit of this embodiment.
Figure 8B:
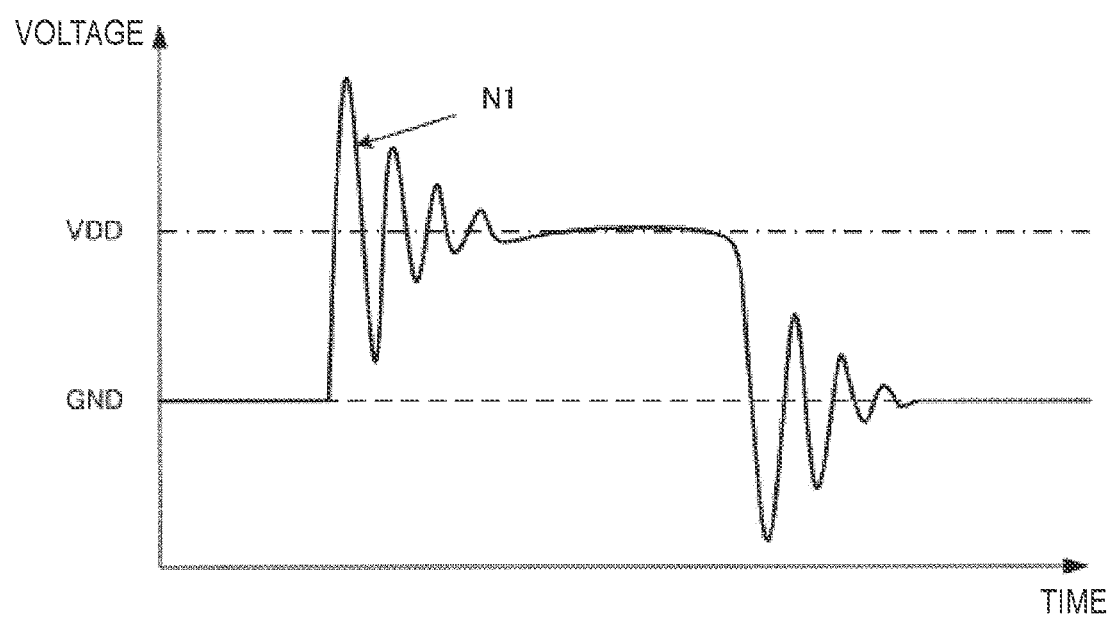
FIG. 8B is a graph showing an output voltage waveform example of a switching circuit of a comparative example.

FIG. 8A is a graph showing an output voltage waveform example of the switching circuit 230 of this embodiment, and FIG. 8B is a graph showing an output voltage waveform example of a switching circuit of a comparative example. The switching circuit of the comparative example is a circuit in which all wirings constituting the electrical loop including the first transistor M1, the second transistor M2, and the capacitor C1 are formed in the first wiring layer, and electrical connection is the same as the circuit diagram shown in FIG. 3. An output voltage waveform is a voltage waveform which is measured on a node corresponding to the first node N1.

In the output voltage waveform example of the comparative example shown in FIG. 8B, ringing occurs at the time of the rising and falling of the voltage waveform. In the output voltage waveform example of this embodiment shown in FIG. 8A, the occurrence of ringing is reduced by various actions described above.

As in this embodiment, when the liquid ejecting apparatus 100 which can eject a liquid with high precision is applied to a printing apparatus (ink jet printer 10), it is possible to implement a printing apparatus having excellent printing quality.

4. First Modification of Arrangement Example of Switching Circuit

The same parts as the foregoing embodiment are represented by the same reference numerals, and detailed description thereof will not be repeated.

Figure 9:
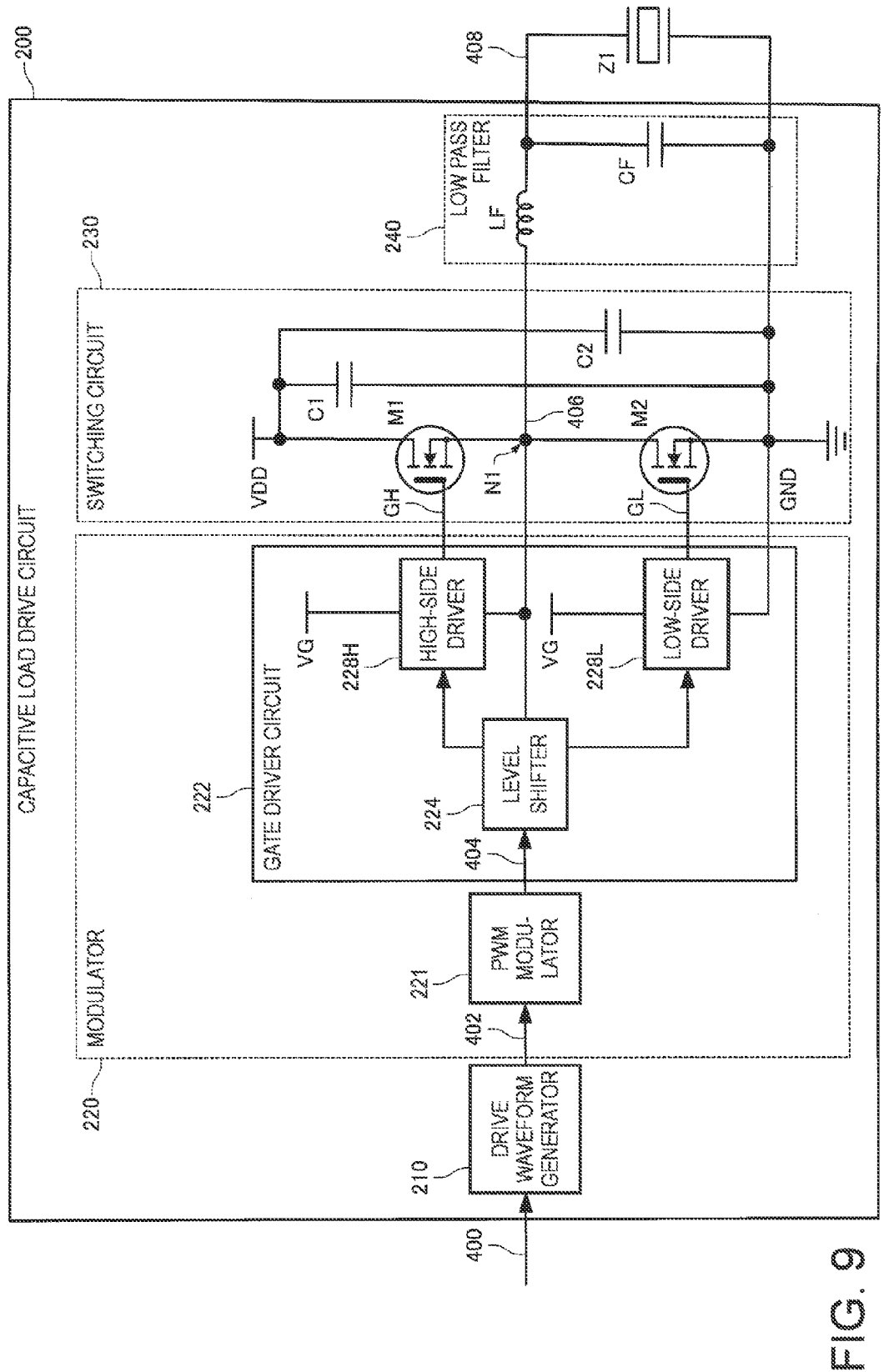
FIG. 9 is an explanatory view showing the detailed configuration of a capacitive load drive circuit of a first modification.

FIG. 9 is an explanatory view showing the detailed configuration of a capacitive load drive circuit 200 of a first modification. When comparing with the example shown in FIG. 3, in the example shown in FIG. 9, there is a difference in that a capacitor C2 is further provided in parallel to the capacitor C1, and other parts are the same as those of the capacitive load drive circuit 200 shown in FIG. 3. The configuration shown in FIG. 9 is advantageous compared to the configuration shown in FIG. 3 in that the capacitance of the bypass capacitor can increase.

Figure 10A:
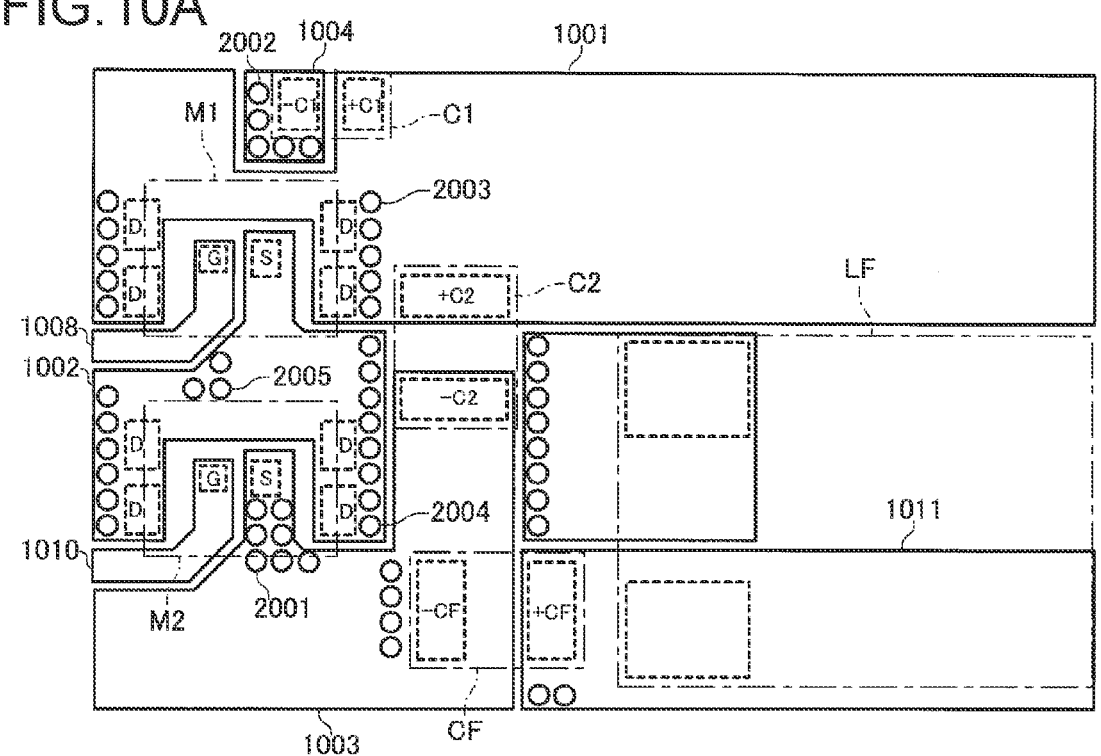
FIGS. 10A and 10B are plan views showing a first modification of an arrangement example of the switching circuit.
Figure 10B:
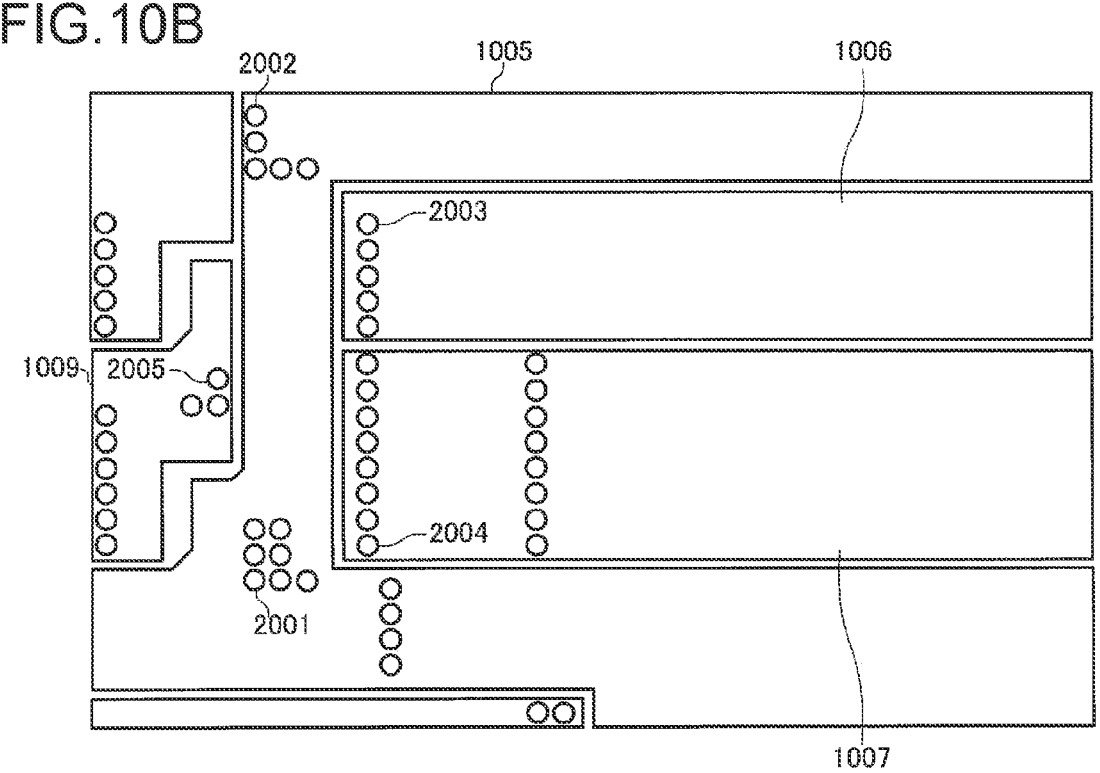

FIGS. 10A and 10B are plan views showing a first modification of the arrangement example of the switching circuit 230. FIG. 10A primarily shows the configuration of the first wiring layer. FIG. 10B primarily shows the configuration of the second wiring layer. In FIGS. 10A and 10B, a solid polygon represents a wiring formed in the first wiring layer or the second wiring layer, and a solid circle represents the position of a via conductor which electrically connects a wiring of the first wiring layer and a wiring of the second wiring layer. In FIG. 10A, a one-dot-chain line represents the mounting position of each transistor, the capacitor, or the coil, and a dotted line represents the position of an electrode of each transistor, the capacitor, or the coil.

In the example shown in FIG. 10A, a first electrode +C2 of the capacitor C2 is electrically connected to the first wiring 1001, and a second electrode −C2 of the capacitor C2 is electrically connected to the third wiring 1003. Other parts are the same as those in the example shown in FIGS. 5A and 5B.

In this configuration, the same effects are also obtained by the same reasons as in the foregoing embodiment.

5. Second Modification of Arrangement Example of Switching Circuit

The same parts as those in the foregoing embodiment and the first modification are represented by the same reference numerals, and detailed description thereof will not be repeated. The circuit configuration of a capacitive load drive circuit 200 in a second modification is the configuration shown in FIG. 9.

Figure 11A:
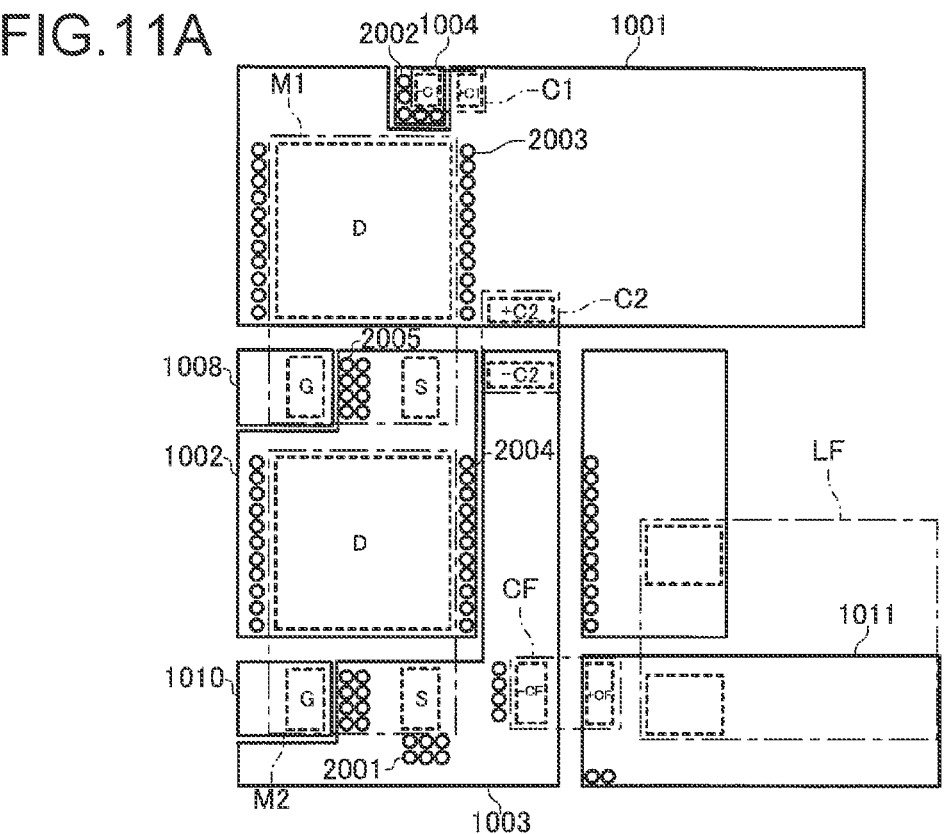
FIGS. 11A and 11B are plan views showing a second modification of an arrangement example of the switching circuit.
Figure 11B:
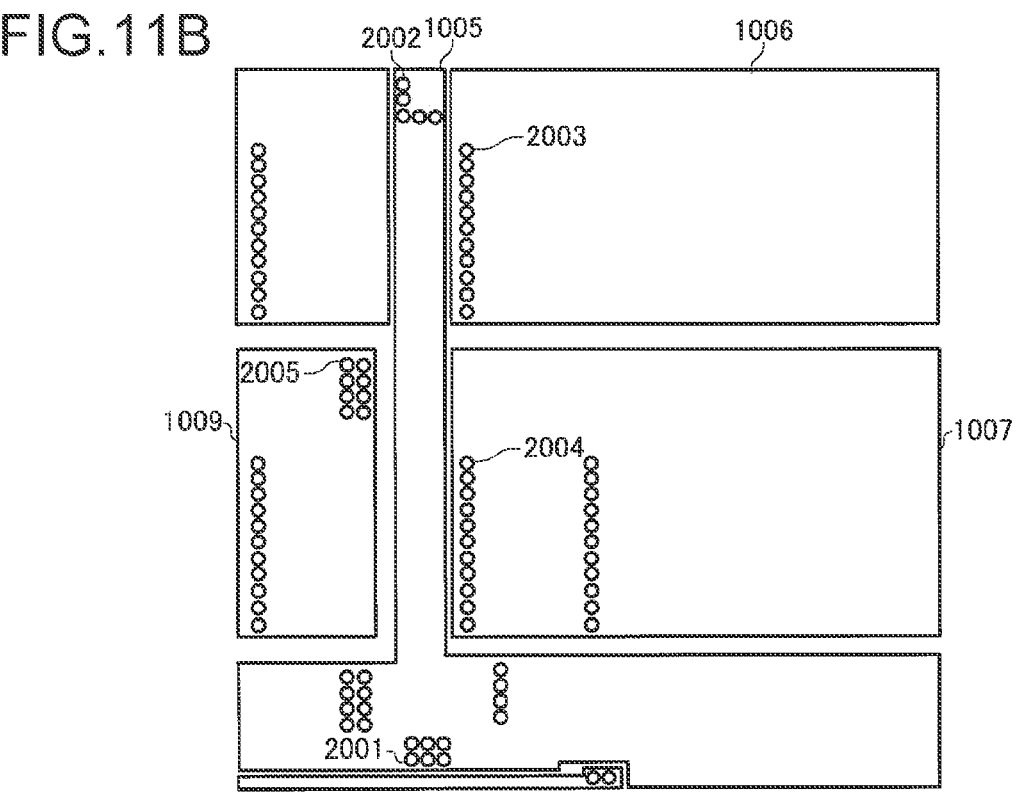

FIGS. 11A and 11B are plan views showing a second modification of the arrangement example of the switching circuit 230. FIG. 11A primarily shows the configuration of the first wiring layer. FIG. 11B primarily shows the configuration of the second wiring layer. In FIGS. 11A and 11B, a solid polygon represents a wiring formed in the first wiring layer or the second wiring layer, and a solid circle represents the position of a via conductor which electrically connects a wiring of the first wiring layer and a wiring of the second wiring layer. In FIG. 11A, a one-dot-chain line represents the mounting position of each transistor, the capacitor, or the coil, and a dotted line represents the position of an electrode of each transistor, the capacitor, or the coil.

When comparing the first modification and the second modification, the arrangement of each electrode of the first transistor M1 and the second transistor M2 is different, and other parts are the same.

In this configuration, the same effects are also obtained by the same reasons as in the foregoing embodiment.

6. Third Modification of Arrangement Example of Switching Circuit

A switching circuit 230 in a third modification includes a multilayer wiring board 1000 having a first wiring layer and a second wiring layer, and a first transistor M1, a second transistor M2, and a capacitor C1 which are mounted on the first wiring layer side of the multilayer wiring board 1000. The circuit configuration of a capacitive load drive circuit 200 in the third modification is the configuration shown in FIG. 3.

Figure 12A:
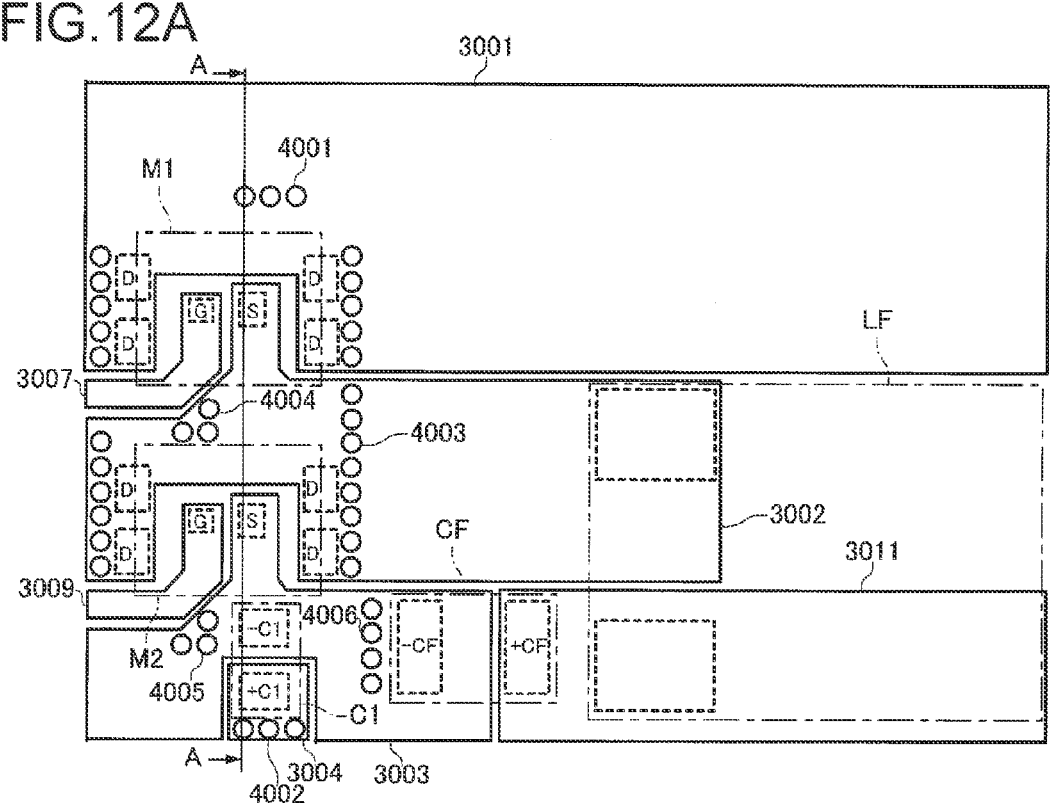
FIGS. 12A and 12B are plan views showing a third modification of an arrangement example of the switching circuit.
Figure 12B:
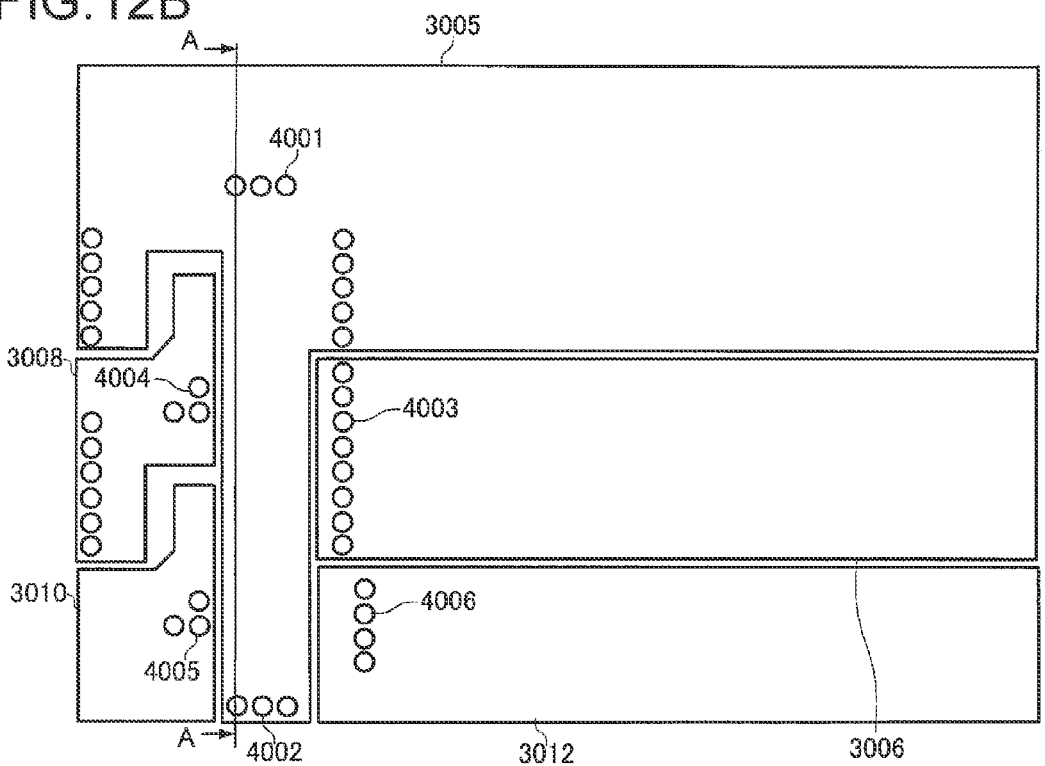

FIGS. 12A and 12B are plan views showing a third modification of the arrangement example of the switching circuit 230. FIG. 12A primarily shows the configuration of the first wiring layer. FIG. 12B primarily shows the configuration of the second wiring layer. In FIGS. 12A and 12B, a solid polygon represents a wiring formed in the first wiring layer or the second wiring layer, and a solid circle represents the position of a via conductor which electrically connects a wiring of the first wiring layer and a wiring of the second wiring layer. In FIG. 12A, a one-dot-chain line represents the mounting position of each transistor, the capacitor, or the coil, and a dotted line represents the position of an electrode of each transistor, the capacitor, or the coil.

Figure 13:
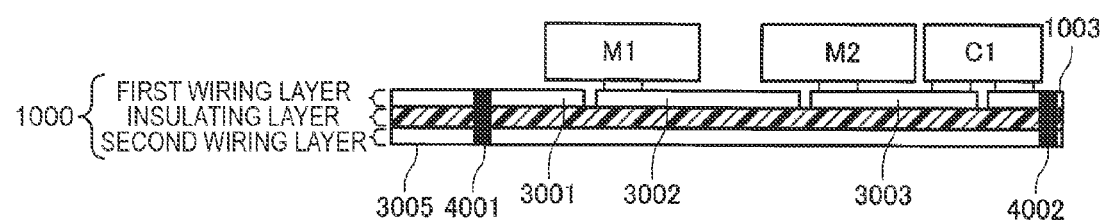
FIG. 13 is a sectional view taken along the line A-A of FIGS. 12A and 12B.

FIG. 13 is a sectional view taken along the line A-A of FIGS. 12A and 12B. As shown in FIG. 13, an insulating layer is provided between the first wiring layer and the second wiring layer of the multilayer wiring board 1000. That is, a wiring formed in the first wiring layer and a wiring formed in the second wiring layer are insulated from each other, except for connection by a via conductor. Usually, the thickness of the insulating layer is sufficiently smaller than the wiring width. The multilayer wiring board 1000 may have three or more wiring layers, and two wiring layers arbitrarily selected from among the three or more wiring layers may be the first wiring layer and the second wiring layer. It is preferable that the first wiring layer and the second wiring layer are wiring layers closest to each other. The multilayer wiring board 1000 may have a protective layer which protects a wiring layer.

The multilayer wiring board 1000 in the third modification has a first wiring 3001, a second wiring 3002, a third wiring 3003, and a fourth wiring 3004 formed in the first wiring layer, a fifth wiring 3005 formed in the second wiring layer, a first via conductor 4001 which electrically connects the first wiring 3001 and the fifth wiring 3005, and a second via conductor 4002 which electrically connects the fourth wiring 3004 and the fifth wiring 3005.

A drain electrode D of the first transistor M1 is electrically connected to the first wiring 3001, and a source electrode S of the first transistor M1 is electrically connected to the second wiring 3002. A drain electrode D of the second transistor M2 is electrically connected to the second wiring 3002, and a source electrode S of the second transistor M2 is electrically connected to the third wiring 3003. A first electrode +C1 of the capacitor C1 is electrically connected to the fourth wiring 3004, and a second electrode −C1 of the capacitor C1 is electrically connected to the third wiring 3003. That is, a part of a wiring path from the drain electrode D of the first transistor M1 to the first electrode +C1 of the capacitor C1 is formed as the fifth wiring 3005 of the second wiring layer.

According to the third modification, since the first transistor M1, the second transistor M2, and the capacitor C1 are all mounted on the first wiring layer side of the multilayer wiring board 1000, and form an electrical loop through the fifth wiring 3005 formed in the second wiring layer, the area of the electrical loop significantly depends on the inter-layer distance between the first wiring layer and the second wiring layer, that is, the thickness of the insulating layer. Accordingly, even if the capacitor C1 increases, it is possible to suppress an increase in the area of the electrical loop including the first transistor M1, the second transistor M2, and the capacitor C1 compared to a case where the capacitor C1 is mounted on the second wiring layer side of the multilayer wiring board 1000. Since the thickness of the insulating layer is sufficiently smaller than the wiring width, it is possible to suppress an increase in the area of the electrical loop including the first transistor M1, the second transistor M2, and the capacitor C1 compared to a case where all wirings are formed in the same wiring layer. That is, it is possible to suppress an increase in parasitic inductance. Accordingly, it is possible to suppress ringing of the output voltage of the switching circuit 230. Therefore, it is possible to implement the liquid ejecting apparatus 100 which can eject a liquid with high precision.

Since the first transistor M1, the second transistor M2, and the capacitor C1 are all mounted on the first wiring layer side of the multilayer wiring board 1000, it is possible to easily perform mounting.

Since there are no elements arranged on the second wiring layer side of the multilayer wiring board 1000, it becomes easy to take heat radiation measures of the first transistor M1 and the second transistor M2, for example, a heat sink on the second wiring layer side of the multilayer wiring board 1000.

In the example shown in FIG. 12A, when the multilayer wiring board 1000 is viewed in plan view, at least a part of the first transistor M1, at least a part of the second transistor M2, and at least a part of the capacitor C1 are arranged on the same line. In the example shown in FIGS. 12A and 13, the first transistor M1, the second transistor M2, and the capacitor C1 are arranged on the same line in this order.

According to the third modification, since at least a part of the first transistor M1, at least a part of the second transistor M2, and at least a part of the capacitor C1 are arranged on the same line, it is possible to decrease the area of the electrical loop including the first transistor M1, the second transistor M2, and the capacitor C1. Accordingly, since it is possible to decrease parasitic inductance, it is possible to suppress ringing of the output voltage of the switching circuit 230. Therefore, it is possible to implement the liquid ejecting apparatus 100 which can eject a liquid with high precision.

In the example shown in FIGS. 12A and 12B, the second wiring 3002 and the fifth wiring 3005 are formed at positions at least partially overlapping each other when the multilayer wiring board 1000 is viewed in plan view.

Usually, reverse currents flow in the second wiring 3002 and the fifth wiring 3005. According to the third modification, since the second wiring 3002 and the fifth wiring 3005 are formed at positions at least partially overlapping each other, parasitic inductance decreases by the effect of mutual inductance described referring to FIG. 7. Accordingly, it is possible to suppress ringing of the output voltage of the switching circuit 230. Therefore, it is possible to implement the liquid ejecting apparatus 100 which can eject a liquid with high precision.

In the example shown in FIGS. 12A and 12B, the multilayer wiring board 1000 further has a sixth wiring 3006 formed in a wiring layer other than the first wiring layer, and a third via conductor 4003 which electrically connects the second wiring 3002 and the sixth wiring 3006.

According to the third modification, since the sixth wiring 3006 electrically connected to the second wiring 3002 is formed in a wiring layer (for example, the second wiring layer) other than the first wiring layer, the sixth wiring 3006 functions as a heat sink. Accordingly, it is possible to improve heat radiation efficiency of the second transistor M2.

In the example shown in FIGS. 12A and 12B, the multilayer wiring board 1000 further has a seventh wiring 3007 formed in the first wiring layer, an eighth wiring 3008 formed in the second wiring layer, and a fourth via conductor 4004 which electrically connects the second wiring 3002 and the eighth wiring 3008, a gate electrode G of the first transistor M1 is electrically connected to the seventh wiring 3007, and the seventh wiring 3007 and the eighth wiring 3008 are formed at positions at least partially overlapping each other when the multilayer wiring board 1000 is viewed in plan view.

Usually, reverse currents flow in the seventh wiring 3007 and the eighth wiring 3008. According to the third modification, since the seventh wiring 3007 and the eighth wiring 3008 are formed at positions at least partially overlapping each other, parasitic inductance decreases by the effect of mutual inductance described referring to FIG. 7. Accordingly, it is possible to suppress ringing of the output voltage of the switching circuit 230. Therefore, it is possible to implement the liquid ejecting apparatus 100 which can eject a liquid with high precision.

In the example shown in FIGS. 12A and 12B, the multilayer wiring board 1000 further has a ninth wiring 3009 formed in the first wiring layer, a tenth wiring 3010 formed in the second wiring layer, and a fifth via conductor 4005 which electrically connects the third wiring 3003 and the tenth wiring 3010, a gate electrode G of the second transistor M2 is electrically connected to the ninth wiring 3009, and the ninth wiring 3009 and the tenth wiring 3010 are formed at positions at least partially overlapping each other when the multilayer wiring board 1000 is viewed in plan view.

Usually, reverse currents flow in the ninth wiring 3009 and the tenth wiring 3010. According to the third modification, since the ninth wiring 3009 and the tenth wiring 3010 are formed at positions at least partially overlapping each other, parasitic inductance decreases by the effect of mutual inductance described referring to FIG. 7. Accordingly, it is possible to suppress ringing of the output voltage of the switching circuit 230. Therefore, it is possible to implement the liquid ejecting apparatus 100 which can eject a liquid with high precision.

In the example shown in FIGS. 12A and 12B, the multilayer wiring board 1000 further has an eleventh wiring 3011 which is formed in the first wiring layer and electrically connected to the first electrode +CF (the positive potential-side electrode) of the capacitor CF, a twelfth wiring 3012 formed in the second wiring layer, and a sixth via conductor 4006 which electrically connects the third wiring 3003 and the twelfth wiring 3012, and the eleventh wiring 3011 and the twelfth wiring 3012 are formed at positions at least partially overlapping each other when the multilayer wiring board 1000 is viewed in plan view.

When common mode noise lies on the output signal of the capacitive load drive circuit 200, a component of common mode noise appears as a current component in the same direction in the eleventh wiring 3011 and the twelfth wiring 3012. According to the third modification, since the eleventh wiring 3011 and the twelfth wiring 3012 are formed at positions at least partially overlapping each other, the effect of mutual inductance described referring to FIG. 7 acts in a direction of cancelling common mode noise. Accordingly, it is possible to suppress common mode noise. It is also possible to suppress EMI noise due to common mode noise.

In this way, in the third modification, as in the output voltage waveform example shown in FIG. 8A, the occurrence of ringing is reduced by various actions described above.

As in the third modification, when the liquid ejecting apparatus 100 which can eject a liquid with high precision is applied to a printing apparatus (ink jet printer 10), it is possible to implement a printing apparatus having excellent printing quality.

7. Fourth Modification of Arrangement Example of Switching Circuit

The same parts as those in the foregoing third modification are represented by the same reference numerals, and detailed description thereof will not be repeated. The circuit configuration of the capacitive load drive circuit 200 in the fourth modification is the configuration shown in FIG. 9.

Figure 14A:
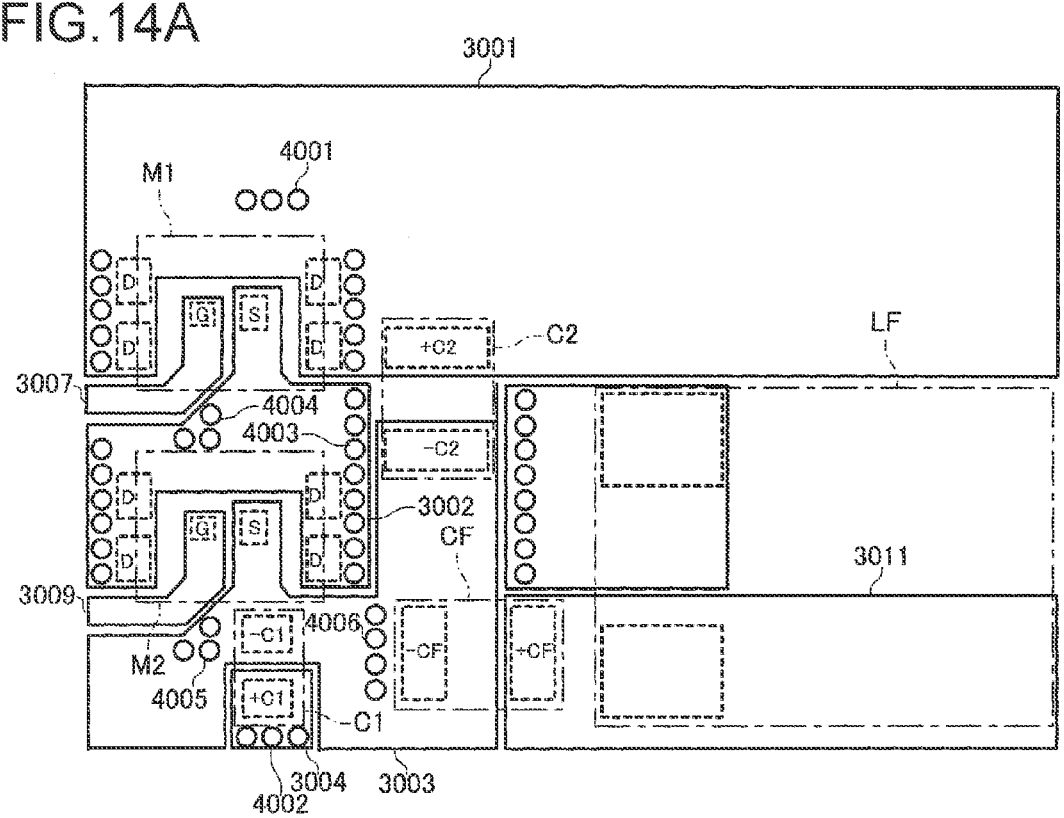
FIGS. 14A and 14B are plan views showing a fourth modification of an arrangement example of the switching circuit.
Figure 14B:
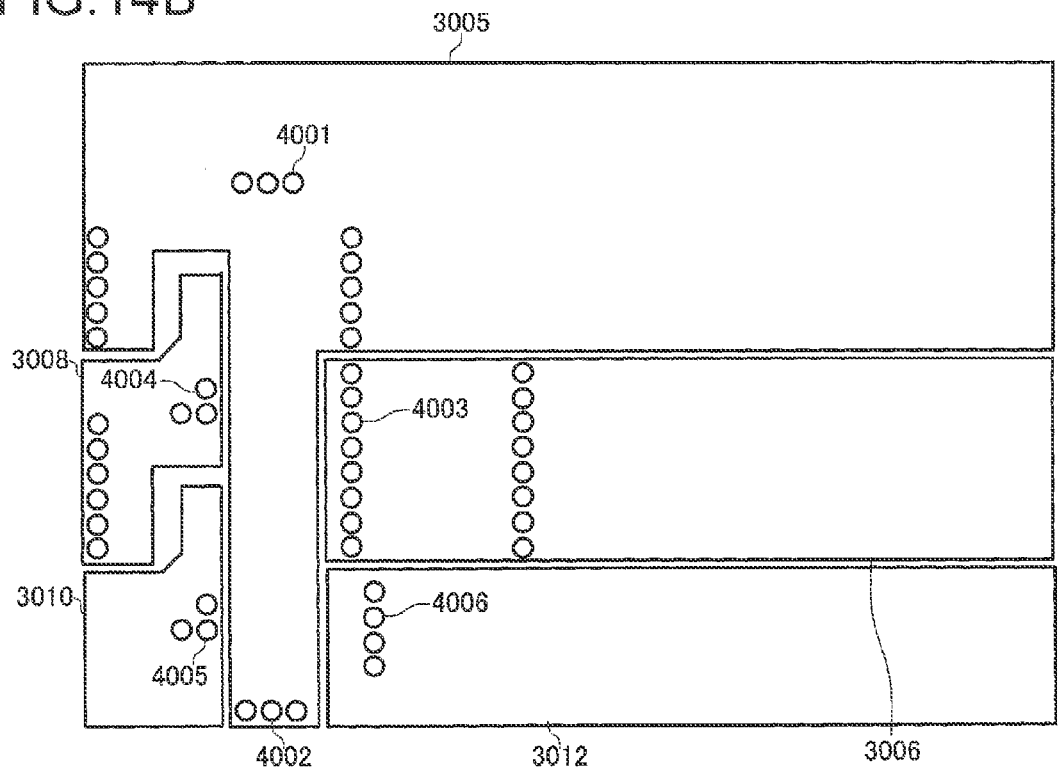

FIGS. 14A and 14B are plan views showing a fourth modification of the arrangement example of the switching circuit 230. FIG. 14A primarily shows the configuration of the first wiring layer. FIG. 14B primarily shows the configuration of the second wiring layer. In FIGS. 14A and 14B, a solid polygon represents a wiring formed in the first wiring layer or the second wiring layer, and a solid circle represents the position of a via conductor which electrically connects a wiring of the first wiring layer and a wiring of the second wiring layer. In FIG. 14A, a one-dot-chain line represents the mounting position of each transistor, the capacitor, or the coil, and a dotted line represents the position of an electrode of each transistor, the capacitor, or the coil.

In the example shown in FIG. 14A, a first electrode +C2 of the capacitor C2 is electrically connected to the first wiring 3001, and a second electrode −C2 of the capacitor C2 is electrically connected to the third wiring 3003. Other parts are the same as those in the third modification shown in FIGS. 12A and 12B.

In this configuration, the same effects are obtained by the same reasons as in the foregoing embodiment and the third modification.

8. Fifth Modification of Arrangement Example of Switching Circuit

The same parts as those in the foregoing third modification and fourth modification are represented by the same reference numerals, and detailed description thereof will not be repeated. The circuit configuration of the capacitive load drive circuit 200 in the fifth modification is the configuration shown in FIG. 9.

Figure 15A:
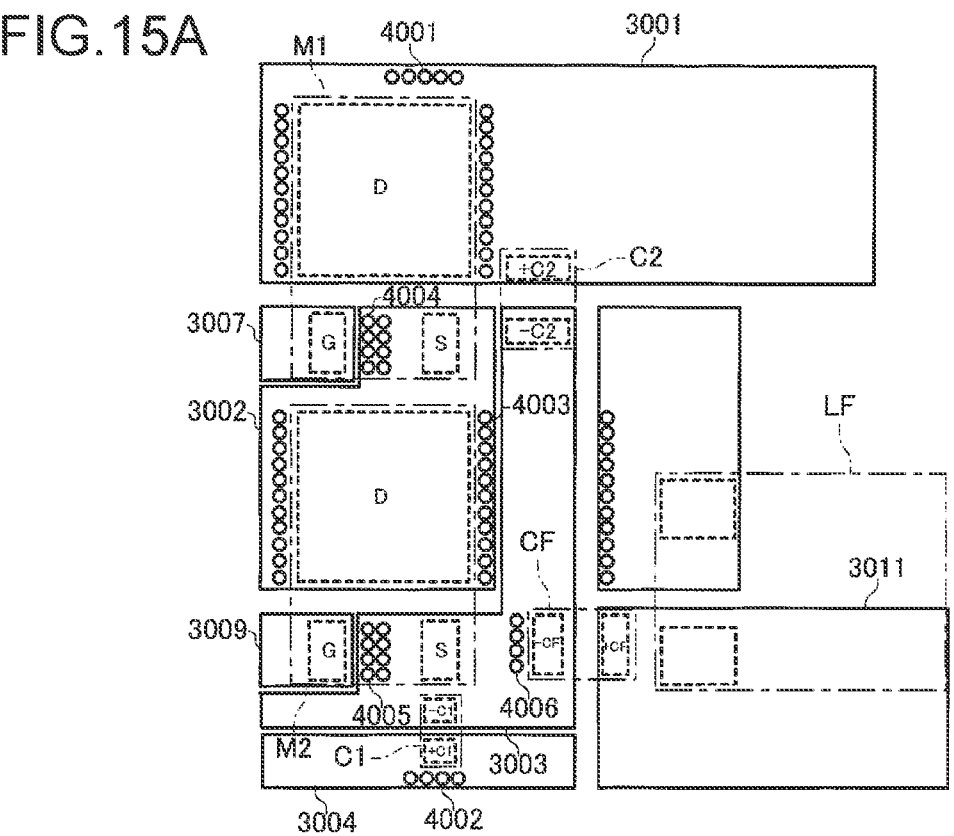
FIGS. 15A and 15B are plan views showing a fifth modification of an arrangement example of the switching circuit.
Figure 15B:
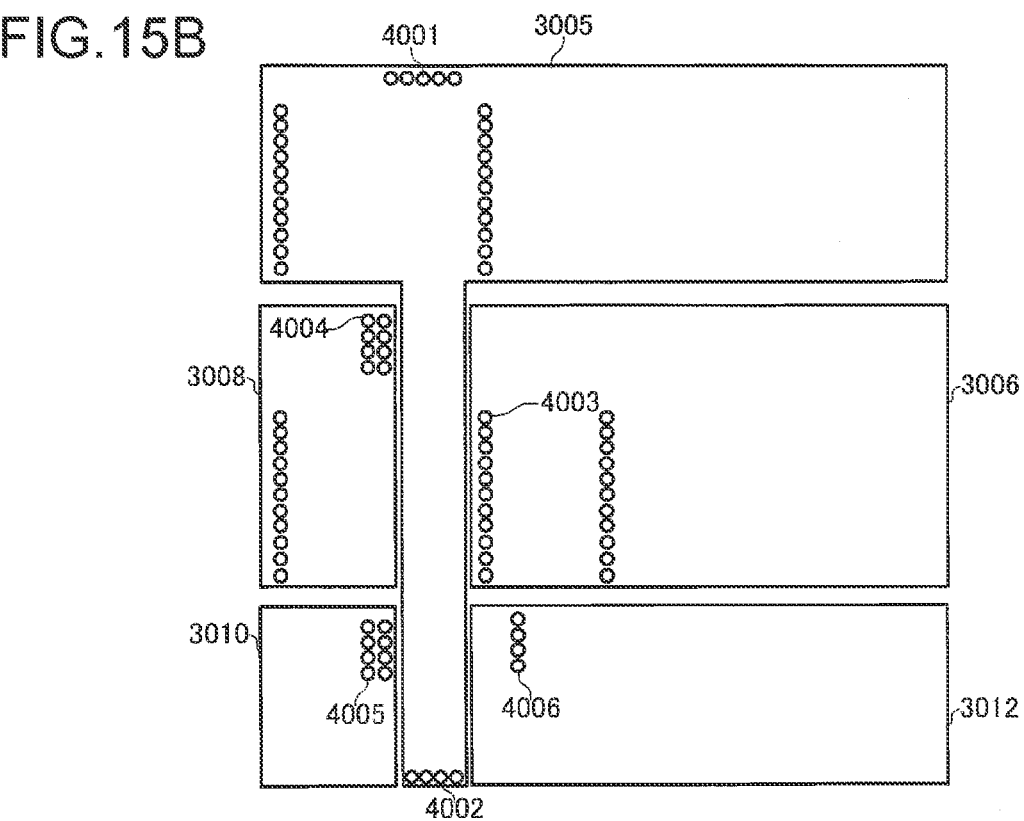

FIGS. 15A and 15B are plan views showing a fifth modification of the arrangement example of the switching circuit 230. FIG. 15A primarily shows the configuration of the first wiring layer. FIG. 15B primarily shows the configuration of the second wiring layer. In FIGS. 15A and 15B, a solid polygon represents a wiring formed in the first wiring layer or the second wiring layer, and a solid circle represents the position of a via conductor which electrically connects a wiring of the first wiring layer and a wiring of the second wiring layer. In FIG. 15A, a one-dot-chain line represents the mounting position of each transistor, the capacitor, or the coil, and a dotted line represents the position of an electrode of each transistor, the capacitor, or the coil.

When comparing the fourth modification and the fifth modification, the arrangement of each electrode of the first transistor M1 and the second transistor M2 is different, and other parts are the same.

In this configuration, the same effects are obtained by the same reasons as in the foregoing embodiment and the third modification.

9. Medical Instrument

The capacitive load drive circuit 200 using the switching circuit 230 is mounted in various medical instruments, thereby increasing reliability of the medical instruments. A fluid ejecting apparatus 1 and a fluid transport apparatus 20 described below are a configuration example included in a liquid ejecting apparatus.

Figure 16:
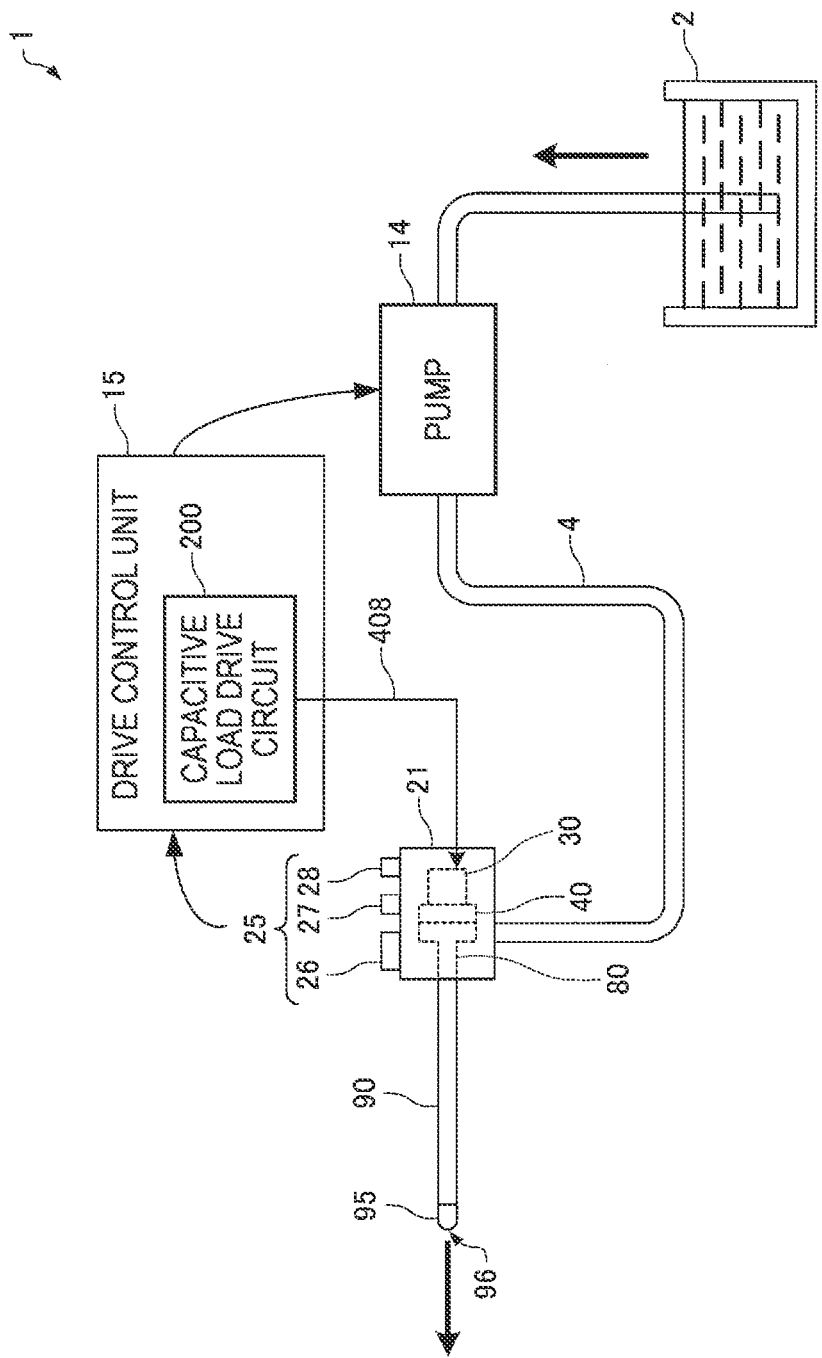
FIG. 16 is an explanatory view illustrating a fluid ejecting apparatus.

For example, the capacitive load drive circuit 200 may be applied as a fluid ejecting apparatus 1. FIG. 16 is an explanatory view illustrating the fluid ejecting apparatus 1. Although the fluid ejecting apparatus 1 is used in various ways for cleaning minute objects and structures and for scalpels, in this case, description will be provided as the fluid ejecting apparatus 1 suitable for operation or treatment of a biological tissue. Accordingly, the fluid is a liquid, for example, water, physiological saline solution, or the like.

In FIG. 16, the fluid ejecting apparatus 1 includes a fluid supply container 2 which stores a fluid, a pump 14 as a fluid supply unit, a pulsation generation unit 21 which converts the fluid supplied from the pump 14 to a pulsation (hereinafter, referred to as a pulse flow), and a drive control unit 15 which controls the driving of the pump 14 and the pulsation generation unit 21. The pump 14 and the pulsation generation unit 21 are connected together by a fluid supply tube 4.

A slender pipe-shaped connection flow path tube 90 is connected to the pulsation generation unit 21, and a nozzle 95 which has a fluid ejection opening 96 with a reduced flow path diameter is inserted into the leading end of the connection flow path tube 90. The connection flow path tube 90 has rigidity so as not to be deformed at the time of fluid ejection.

The pulsation generation unit 21 has an ejection command switching unit 25, and in this embodiment, as the ejection command switching unit 25, a pulse flow command switch 26 which is used to select pulse flow ejection, a continuous flow command switch 27 which is used to select continuous flow ejection, and an OFF switch 28 which is used to stop fluid ejection are provided.

The flow of the fluid in the fluid ejecting apparatus 1 configured as above will be simply described. The fluid stored in the fluid supply container 2 is sucked by the pump 14 and supplied to the pulsation generation unit 21 through the fluid supply tube 4 at a given pressure. The pulsation generation unit 21 is provided with a fluid chamber 80 (see FIG. 17 described below), and a piezoelectric element 30 and a diaphragm 40 as a volume change unit which changes the volume of the fluid chamber 80. The piezoelectric element 30 is driven to generate a pulsation inside the fluid chamber 80, and the fluid is ejected at high speed in a pulsed form from the fluid ejection opening 96 through the connection flow path tube 90 and the nozzle 95.

When the driving of the pulsation generation unit 21 stops, the fluid supplied from the pump 14 is ejected in a continuous flow from the fluid ejection opening 96 through the fluid chamber 80.

The pulsation means the flow of a fluid in which the flow direction of the fluid is kept constant and the flow rate or velocity of the fluid fluctuates periodically or irregularly. Although the pulsation includes an intermittent flow in which the fluid repeatedly flows and stops, the pulsation may not be a intermittent flow insofar as the flow rate or velocity of the fluid fluctuates periodically or irregularly.

Similarly, the pulsed ejection of the fluid means the ejection of the fluid in which the flow rate or velocity of the fluid to be ejected fluctuates periodically or irregularly. Although an example of the pulsed ejection includes intermittent ejection in which the ejection and non-ejection of the fluid are repeated, the pulsed ejection may not be intermittent ejection insofar as the flow rate or velocity of the fluid to be ejected fluctuates periodically or irregularly.

Figure 17:
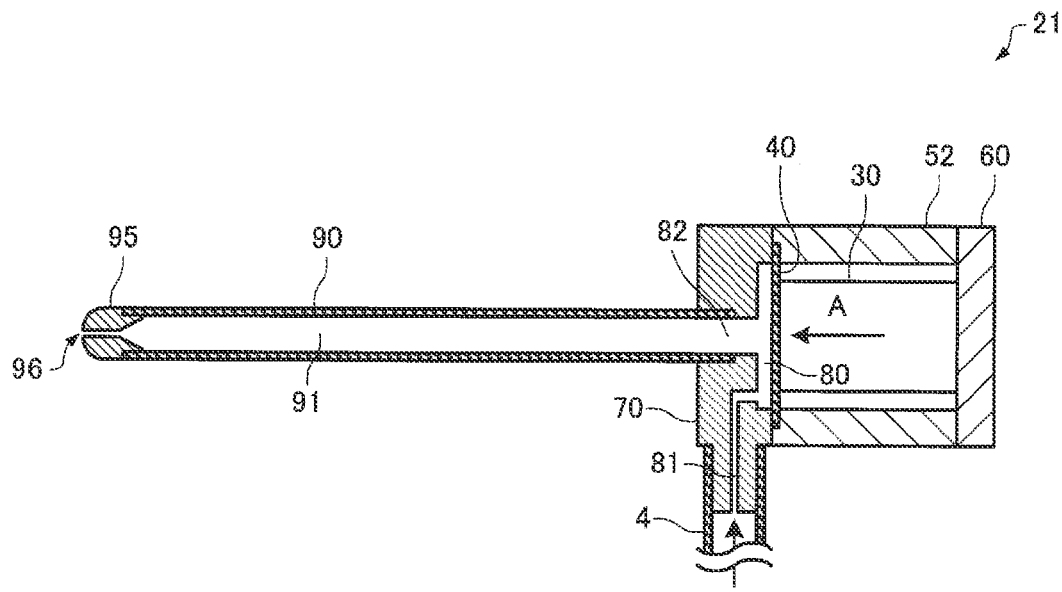
FIG. 17 is a sectional view showing a cut section when a pulsation generation unit of this embodiment is cut along a fluid ejection direction.

FIG. 17 is a sectional view of the pulsation generation unit 21 of this embodiment taken along the ejection direction of the fluid. In FIG. 17, the scale of each member or portion is adjusted for convenience of illustration. The pulsation generation unit 21 has an entrance flow path 81 which supplies the fluid from the pump 14 to the fluid chamber 80 through the fluid supply tube 4, a piezoelectric element 30 and a diaphragm 40 as a volume change unit which changes the volume of the fluid chamber 80, and an exit flow path 82 which communicates with the liquid chamber 80. The fluid supply tube 4 is connected to the entrance flow path 81.

The diaphragm 40 is made of, for example a disk-like sheet metal, and comes into close contact with a case 52 by a case 70. In regard to the piezoelectric element 30, in this embodiment, a laminated piezoelectric element is illustrated, and one of both ends is fixed to the diaphragm 40 and the other end is fixed to a bottom plate 60.

The fluid chamber 80 is a space which is formed by a concave portion formed in a surface of the case 70 facing the diaphragm 40 and the diaphragm 40. The exit flow path 82 is formed substantially in the central portion of the fluid chamber 80.

The case 70 and the case 52 are bonded together as a single body in opposing surfaces. A connection flow path tube 90 having a connection path 91 communicating with the exit flow path 82 is fitted into the case 70, and the nozzle 95 is inserted into the leading end of the connection flow path tube 90. The fluid ejection opening 96 with a reduced flow path diameter is formed in the nozzle 95.

The piezoelectric element 30 corresponds to the capacitive load Z1 of FIG. 1, and the deformation amount or timing is controlled by the drive signal 408 (see FIG. 16) of the capacitive load drive circuit 200. The fluid chamber 80 is pressed in a direction of arrow A of FIG. 17, whereby the fluid can be ejected in a pulsed form from the nozzle 95 at the leading end. The fluid ejecting apparatus 1 is used as, for example, a medical apparatus. Specifically, the fluid ejecting apparatus 1 may be used as a surgical apparatus which supplies a liquid at a high pressure from the pump 14 to the fluid supply tube 4 to be introduced into a body cavity and ejects the liquid from the nozzle 95 at the leading end to cut a tissue in the body cavity by a fluid pressure.

The capacitive load drive circuit 200 may be applied as the fluid transport apparatus 20 which transports the fluid at a stable flow rate.

Figure 18:
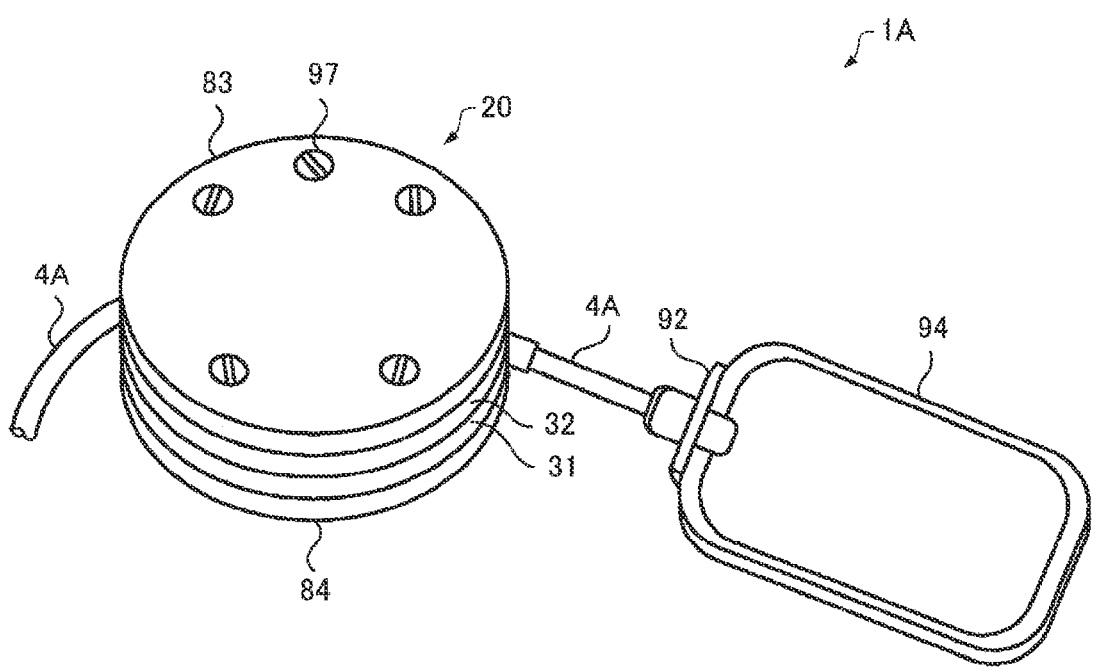
FIG. 18 is a perspective view showing the appearance of a fluid transporter including a fluid transport apparatus of this embodiment.

FIG. 18 is a perspective view showing the appearance of a fluid transporter 1A including the fluid transport apparatus 20 of this embodiment. In FIG. 18, the fluid transporter 1A includes the fluid transport apparatus 20 which transports the fluid by peristaltic motion, and a pack-shaped fluid storage container 94 which stores the fluid. The fluid transport apparatus 20 and the fluid storage container 94 communicate with each other by a tube 4A.

The fluid storage container 94 is made of flexible synthetic resin, for example, silicon-based resin. A tube holder 92 is provided at one end of the fluid storage container 94, and the tube 4A is fixed airtight by crimping, thermal welding, or adhesion such that the fluid does not leak.

The tube 4A communicates with the inside of the fluid storage container 94 at one end, passes through the fluid transport apparatus 20, and extends outside the fluid transport apparatus 20, and the fluid stored in the fluid storage container 94 is transported to the outside by the fluid transport apparatus 20.

The fluid transport apparatus 20 has a structure in which a lower lid 84, a pump unit frame 31, a tube frame 32, and an upper lid 83 are stacked sequentially and integrated by fixing screws 97 (in the drawing, upper lid fixing screws are shown) or the like. An extrusion mechanism which transports the fluid into is accommodated in the fluid transport apparatus 20.

When the fluid transporter 1A is put on a biological object, it is preferable that the lower lid 84, the pump unit frame 31, the tube frame 32, the upper lid 83, and the fluid storage container 94 are made of a material having excellent biocompatibility, for example, synthetic resin, such as polysulphone or urethane.

Figure 19:
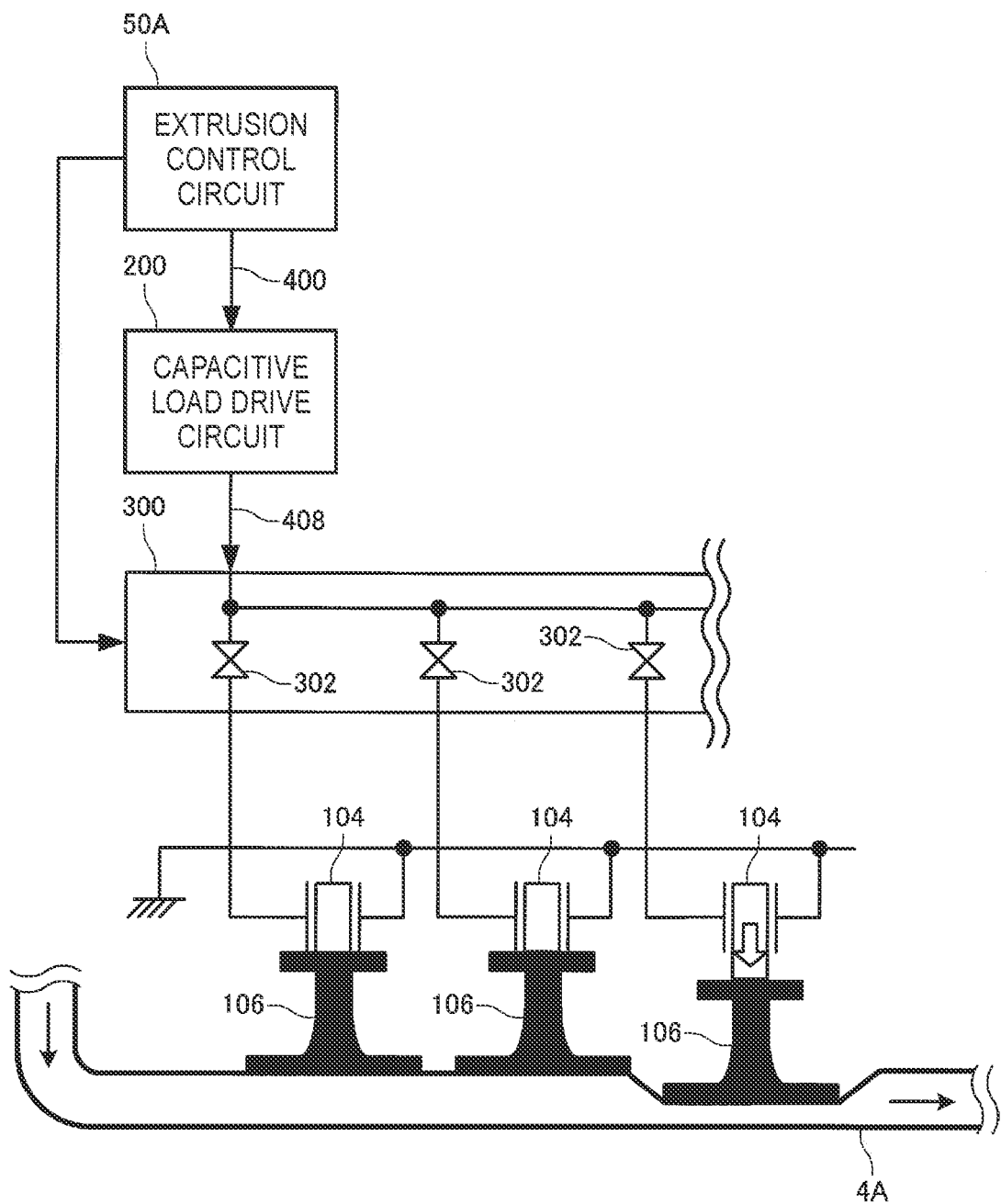
FIG. 19 is a diagram illustrating a fluid transport mechanism of the fluid transport apparatus.

FIG. 19 is a diagram illustrating a fluid transport mechanism of the fluid transport apparatus 20. The drive signal 408 which is a voltage to be applied to the piezoelectric element 104 is generated on the basis of the control signal 400 from the extrusion control circuit 50A (not shown in FIG. 18) by the capacitive load drive circuit 200. The generated drive signal 408 is supplied to the piezoelectric element 104 through the gate unit 300. The gate unit 300 is a circuit unit which a plurality of gate elements 302 are connected in parallel, and each gate element 302 can be individually placed in a conduction state or a disconnection state under the control of the extrusion control circuit 50A. Accordingly, the drive signal 408 output from the capacitive load drive circuit 200 passes through the gate elements 302 in sequence by the extrusion control circuit 50A and applied to the corresponding piezoelectric element 104, and a corresponding pressing shaft 106 is extruded. The pressing shaft 106 is arranged perpendicular to the flow direction of the fluid in the tube 4A. The tube 4A is pressed in sequence by a plurality of pressing shafts 106. For this reason, the fluid transport apparatus 20 can transport the fluid in the tube 4A by peristaltic motion.

As a fluid which is used in the invention, in addition to liquids having fluidity, such as water, saline, chemicals, oils, fragrant liquids, and ink, gas may be used. For example, when chemical is used, the fluid transport apparatus 20 may be used as a medication pump.

In this way, according to the medical instrument of this embodiment, since the switching circuit 230 in which the occurrence of ringing is suppressed is provided, it is possible to implement a medical instrument which can stably handle a fluid.

The foregoing embodiments and modifications are just an example, and the invention is not limited thereto. For example, the embodiments and the modifications may be appropriately carried out in combination.

The invention is not limited to the foregoing embodiments and modifications, and may be modified in various ways. For example, the invention includes substantially the same configuration (for example, a configuration having the same functions, methods, and results, or a configuration having the same objects and effects) as the configuration described in the foregoing embodiments and the modifications. The invention includes a configuration in which a non-essential portion in the configuration described in the embodiment or the like is substituted. The invention includes a configuration in which the same functional effects as the configuration described in the embodiment or the like are obtained, or a configuration in which the same objects can be attained. The invention includes a configuration in which the known technique is added to the configuration described in the embodiment or the like.

What is claimed is:

1. A medical instrument comprising:
   a drive waveform generator which generates a drive waveform signal;
   a modulator which performs pulse modulation on the drive waveform signal to generate a modulated signal;
   a multilayer wiring board having:
     a first wiring, a second wiring, a third wiring, and a fourth wiring formed in a first wiring layer,
     a fifth wiring formed in a second wiring layer,
     a first via conductor electrically connecting the third wiring and the fifth wiring, and
     a second via conductor electrically connecting the fourth wiring and the fifth wiring;
   a first transistor, a second transistor, and a capacitor mounted on the first wiring layer side of the multilayer wiring board,
   wherein the drain electrode of the first transistor is electrically connected to the first wiring, the source electrode of the first transistor is electrically connected to the second wiring, the drain electrode of the second transistor is electrically connected to the second wiring, the source electrode of the second transistor is electrically connected to the third wiring, the first electrode of the capacitor is electrically connected to the first wiring, and the second electrode of the capacitor is electrically connected to the fourth wiring,
   wherein, when the multilayer wiring board is viewed in plan view, at least a part of the first transistor, at least a part of the second transistor, and at least a part of the capacitor are arranged on the same line, and
   wherein the second wiring and the fifth wiring are formed at positions at least partially overlapping each other when the multilayer wiring board is viewed in plan view, and
   wherein the multilayer wiring board receives the modulated signal on a gate electrode of the first transistor and a gate electrode of the second transistor, and generates an amplified digital signal as a signal obtained through power amplification on the modulated signal; and
   a low pass filter which smoothes the amplified digital signal to generate a drive signal.

2. The medical instrument according to claim 1, wherein the multilayer wiring board further has a sixth wiring formed in a wiring layer other than the first wiring layer, and a third via conductor electrically connecting the first wiring and the sixth wiring.

3. A medical instrument comprising:
   a drive waveform generator which generates a drive waveform signal;
   a modulator which performs pulse modulation on the drive waveform signal to generate a modulated signal;
   the medical instrument according to claim 2 which receives the modulated signal on the gate electrode of the first transistor and the gate electrode of the second transistor, and generates an amplified digital signal as a signal obtained through power amplification on the modulated signal; and
   a low pass filter which smoothes the amplified digital signal to generate a drive signal.

4. The medical instrument according to claim 1, wherein the multilayer wiring board further has a seventh wiring formed in a wiring layer other than the first wiring layer, and a fourth via conductor electrically connecting the second wiring and the seventh wiring.

5. A medical instrument comprising:
   a drive waveform generator which generates a drive waveform signal;
   a modulator which performs pulse modulation on the drive waveform signal to generate a modulated signal;
   the medical instrument according to claim 4 which receives the modulated signal on the gate electrode of the first transistor and the gate electrode of the second transistor, and generates an amplified digital signal as a signal obtained through power amplification on the modulated signal; and
   a low pass filter which smoothes the amplified digital signal to generate a drive signal.

6. The medical instrument according to claim 4, wherein the multilayer wiring board further has
   an eighth wiring formed in the first wiring layer,
   a ninth wiring formed in the second wiring layer, and
   a fifth via conductor electrically connecting the second wiring and the ninth wiring,
   the gate electrode of the first transistor is electrically connected to the eighth wiring, and
   the eighth wiring and the ninth wiring are formed at positions at least partially overlapping each other when the multilayer wiring board is viewed in plan view.

7. A medical instrument comprising:
   a drive waveform generator which generates a drive waveform signal;
   a modulator which performs pulse modulation on the drive waveform signal to generate a modulated signal;
   the medical instrument according to claim 6 which receives the modulated signal on the gate electrode of the first transistor and the gate electrode of the second transistor, and generates an amplified digital signal as a signal obtained through power amplification on the modulated signal; and
   a low pass filter which smoothes the amplified digital signal to generate a drive signal.

8. The medical instrument according to claim 1, wherein the multilayer wiring board further has a tenth wiring formed in the first wiring layer, the gate electrode of the second transistor is electrically connected to the tenth wiring, and the fifth wiring and the tenth wiring are formed at positions at least partially overlapping each other when the multilayer wiring board is viewed in plan view.

* * * * *